(12) United States Patent
Tian et al.

(10) Patent No.: US 12,157,886 B2
(45) Date of Patent: Dec. 3, 2024

(54) TYPE II CRISPR/CAS9 GENOME EDITING SYSTEM AND THE APPLICATION THEREOF

(71) Applicant: ZHUHAI SHU TONG MEDICAL TECHNOLOGY CO., LTD., Guangdong (CN)

(72) Inventors: Rui Tian, Guangdong (CN); Long Huang, Guangdong (CN); Hongxian Xie, Guangdong (CN)

(73) Assignee: ZHUHAI SHU TONG MEDICAL TECHNOLOGY CO., LTD., Zhuhai (CN)

( * ) Notice: Subject to any disclaimer, the term of this patent is extended or adjusted under 35 U.S.C. 154(b) by 38 days.

(21) Appl. No.: 17/676,546

(22) Filed: Feb. 21, 2022

(65) Prior Publication Data

US 2023/0265421 A1    Aug. 24, 2023

(51) Int. Cl.
| | |
|---|---|
| C12N 9/22 | (2006.01) |
| C12N 15/11 | (2006.01) |
| C12N 15/63 | (2006.01) |
| C12N 15/90 | (2006.01) |

(52) U.S. Cl.
CPC .............. *C12N 15/111* (2013.01); *C12N 9/22* (2013.01); *C12N 15/63* (2013.01); *C12N 15/907* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2016/0130608 A1*  5/2016  Doudna ................... C12N 9/22
                                                            435/462
2022/0307018 A1*  9/2022  Kim .................... C12N 15/907

FOREIGN PATENT DOCUMENTS

| CN | 112331264 A | 2/2021 | |
|---|---|---|---|
| CN | 113851186 A | 12/2021 | |
| WO | WO-2021086083 A2 * | 5/2021 | ........... C12N 15/102 |

OTHER PUBLICATIONS

Cox et al., Uniprot Accession A0A1Q9YNK3 (Year: 2017).*
Ngo et al. in The Protein Folding Problem and Tertiary Structure Prediction, 1994, Merz et al. (ed.), Birkhauser, Boston, MA, pp. 433 and 492-495.*
Gen Li, Prediction of Anti-tracrRNA in Phage, Mar. 15, 2019, https://www.cnki.net.
NCBI Accession No. WP_075884445.1, Jun. 19, 2019.
NCBI Accession No. WP_217947137.1, Mar. 1, 2022.
NCBI Accession No. OLU47462, Jan. 19, 2017.
NCBI Accession No. OLU47412, Jan. 19, 2017.
Xuelian Wang et al., CRISPR-Cas9 System as a Versatile Tool for Genome Engineering in Human Cells, Molecular Therapy-Nucleic Acids, Nov. 15, 2016, pp. 1-9, vol. 5, No. e388.
NCBI Accession No. A0A1Q9YNK3_9FIRM, Apr. 12, 2017.

* cited by examiner

*Primary Examiner* — Richard G Hutson

(57) ABSTRACT

The disclosure relates to a Type II CRISPR/Cas9 genome editing system, belonging to the technical field of genome editing. The genome editing system comprises a Cas9 protein, helper proteins, a CRISPR RNA and a trans-activated CRISPR RNA; wherein the Cas9 protein is a DNA endonuclease, and the Cas9 protein has an amino acid sequence as shown in SEQ ID NO: 1, or an amino acid sequence with at least 80%, 85%, 90%, 95%, 98%, or 99% homology to the amino acid sequence as shown in SEQ ID NO: 1. According to the disclosure, through bioinformatics analysis, the Type II CRSIPR/Cas9 genome editing system in the *Faecalibaculum rodentium* is discovered, and the genome editing system is applied to editing prokaryotic or eukaryotic genes and provides a new selection for a genome editing toolbox.

9 Claims, 14 Drawing Sheets

Specification includes a Sequence Listing.

Fig.9

SEQUENCE LISTING

```
<160> NUMBER OF SEQ ID NOS: 33

<210> SEQ ID NO 1
<211> LENGTH: 1372
<212> TYPE: PRT
<213> ORGANISM: Faecalibaculum rodentium

<400> SEQUENCE: 1

Met Cys Thr Lys Glu Ser Glu Lys Leu Asn Lys Asn Ala Asp Tyr Tyr
1               5                   10                  15

Ile Gly Leu Asp Met Gly Thr Ser Ser Ala Gly Trp Ala Val Ser Asp
            20                  25                  30
```

```
Ser Glu Tyr Asn Leu Ile Arg Arg Lys Gly Lys Asp Leu Trp Gly Val
            35                  40                  45
Arg Gln Phe Glu Glu Ala Lys Thr Ala Ala Glu Arg Arg Gly Phe Arg
 50                  55                  60
Val Ala Arg Arg Arg Lys Gln Arg Gln Val Arg Asn Arg Leu Leu
 65                  70                  75                  80
Ser Glu Glu Phe Gln Asn Glu Ile Thr Lys Ile Asp Ser Gly Phe Leu
                    85                  90                  95
Lys Arg Met Glu Asp Ser Arg Phe Val Ile Ser Asp Lys Arg Val Pro
            100                 105                 110
Glu Lys Tyr Thr Leu Phe Asn Asp Ser Gly Tyr Thr Asp Val Glu Tyr
            115                 120                 125
Tyr Asn Gln Tyr Pro Thr Ile Tyr His Leu Arg Lys Ala Leu Ile Glu
130                 135                 140
Ser Asn Glu Arg Phe Asp Ile Arg Leu Val Phe Leu Gly Ile His Ser
145                 150                 155                 160
Leu Phe Gln His Pro Gly His Phe Leu Asp Lys Gly Asp Val Asp Thr
                    165                 170                 175
Asp Asn Thr Gly Pro Glu Glu Leu Ile Gln Phe Leu Glu Asp Cys Met
            180                 185                 190
Asn Glu Ile Gln Ile Ser Ile Pro Leu Val Ser Asn Gln Lys Val Leu
            195                 200                 205
Thr Asp Ile Leu Thr Asp Ser Arg Ile Thr Arg Arg Asp Lys Glu Gln
            210                 215                 220
Gln Ile Leu Glu Ile Leu Gln Pro Asn Lys Glu Ser Lys Lys Ala Val
225                 230                 235                 240
Ser Gln Phe Val Lys Val Leu Thr Gly Gln Lys Ala Lys Leu Gly Asp
                    245                 250                 255
Leu Ile Met Met Glu Asp Lys Asp Thr Glu Tyr Lys Tyr Ser Phe
            260                 265                 270
Ser Phe Arg Glu Lys Thr Leu Glu Glu Ile Leu Pro Asp Ile Glu Gly
            275                 280                 285
Val Ile Asp Gly Leu Ala Leu Glu Tyr Ile Glu Ser Ile Tyr Ser Leu
            290                 295                 300
Tyr Ser Trp Ser Leu Leu Asn Ser Tyr Met Lys Asp Thr Leu Thr Gly
305                 310                 315                 320
His Tyr Tyr Ser Tyr Leu Ala Glu Ala Arg Val Ala Ala Tyr Asp Lys
                    325                 330                 335
His His Ser Asp Leu Val Lys Leu Lys Thr Leu Phe Arg Glu Tyr Ile
            340                 345                 350
Pro Glu Glu Tyr Asp Asn Phe Phe Arg Lys Met Glu Lys Ala Asn Tyr
            355                 360                 365
Ser His Tyr Ile Gly Ser Thr Glu Tyr Asp Gly Glu Lys Arg Cys Arg
            370                 375                 380
Thr Ala Lys Ala Lys Gln Glu Asp Phe Tyr Lys Ser Ile Asn Lys Met
385                 390                 395                 400
Leu Glu Lys Ile Pro Glu Cys Ser Glu Lys Thr Glu Ile Gln Lys Glu
                    405                 410                 415
Ile Ile Glu Gly Thr Phe Leu Leu Lys Gln Thr Gly Pro Gln Asn Gly
            420                 425                 430
Phe Val Pro Asn Gln Leu Gln Leu Lys Glu Leu Arg Lys Ile Leu Gln
            435                 440                 445
Asn Ala Ser Lys His Tyr Pro Phe Leu Thr Glu Lys Asp Glu Arg Asp
```

```
                  450                 455                 460
Met Thr Ala Ile Asp Arg Ile Glu Ala Leu Phe Ser Phe Arg Ile Pro
465                 470                 475                 480

Tyr Tyr Ile Gly Pro Leu Lys Asn Thr Asp Asn Gln Gly His Gly Trp
                    485                 490                 495

Ala Val Arg Arg Asp Gly His Glu Gln Ile Pro Val Arg Pro Trp Asn
                500                 505                 510

Phe Glu Glu Ile Ile Asp Glu Ser Ala Ser Ala Asp Leu Phe Ile Lys
            515                 520                 525

Asn Leu Val Asn Ser Cys Thr Tyr Leu Arg Thr Glu Lys Val Leu Pro
        530                 535                 540

Lys Ser Ser Leu Leu Tyr Gln Glu Phe Glu Val Leu Asn Glu Leu Asn
545                 550                 555                 560

Asn Leu Arg Ile Asn Gly Met Tyr Pro Asp Glu Ile Gln Pro Gly Leu
                    565                 570                 575

Lys Arg Met Ile Phe Glu Gln Cys Phe Tyr Ser Gly Lys Lys Val Thr
                580                 585                 590

Gly Lys Lys Leu Gln Leu Phe Leu Arg Ser Val Leu Thr Asn Ser Ser
            595                 600                 605

Thr Glu Glu Phe Val Leu Thr Gly Ile Asp Lys Asp Phe Lys Ser Ser
        610                 615                 620

Leu Ser Ser Tyr Lys Lys Phe Cys Glu Leu Phe Gly Val Lys Thr Leu
625                 630                 635                 640

Asn Asp Thr Gln Lys Val Met Ala Glu Gln Ile Ile Glu Trp Ser Thr
                    645                 650                 655

Val Tyr Gly Asp Ser Arg Lys Phe Leu Lys Arg Lys Leu Glu Asp Asn
                660                 665                 670

Tyr Pro Glu Leu Thr Asp Gln Gln Ile Arg Arg Ile Ala Gly Phe Lys
            675                 680                 685

Phe Ser Glu Trp Gly Asn Leu Ser Arg Ala Phe Leu Glu Met Glu Gly
        690                 695                 700

Tyr Lys Asp Glu Ala Gly Asn Pro Val Thr Ile Ile Arg Ala Leu Arg
705                 710                 715                 720

Asp Thr Gln Lys Asn Leu Met Gln Leu Leu Ser Asn Asp Ser Ala Phe
                    725                 730                 735

Ala Lys Lys Leu Gln Glu Leu Asn Asp Tyr Val Thr Arg Asp Ile Trp
                740                 745                 750

Ser Ile Glu Pro Asp Asp Leu Asp Gly Met Tyr Leu Ser Ala Pro Val
            755                 760                 765

Arg Arg Met Ile Trp Gln Thr Phe Leu Ile Leu Arg Glu Val Val Asp
        770                 775                 780

Thr Ile Gly Tyr Ser Pro Lys Lys Ile Phe Met Glu Met Ala Arg Gly
785                 790                 795                 800

Glu Gln Glu Lys Lys Arg Thr Ala Ser Arg Lys Lys Gln Leu Ile Asp
                    805                 810                 815

Leu Tyr Lys Glu Ala Gly Met Lys Asn Asp Glu Leu Phe Gly Asp Leu
                820                 825                 830

Glu Ser Leu Glu Glu Ala Gln Leu Arg Ser Lys Lys Leu Tyr Leu Tyr
            835                 840                 845

Phe Arg Gln Met Gly Arg Asp Ile Tyr Ser Gly Lys Leu Ile Asp Phe
        850                 855                 860

Met Asp Val Leu His Gly Asn Arg Tyr Asp Ile Asp His Ile His Pro
865                 870                 875                 880
```

```
Gln Ser Lys Lys Lys Asp Asp Ser Leu Glu Asn Asn Leu Val Leu Thr
            885                 890                 895

Ser Lys Asp Phe Asn Asn His Ile Lys Gln Asp Val Tyr Pro Ile Pro
            900                 905                 910

Glu Gln Ile Gln Ser Arg Gln Lys Gly Phe Trp Ala Met Leu Leu Lys
            915                 920                 925

Gln Gly Phe Met Ser Gln Glu Lys Tyr Asn Arg Leu Met Arg Thr Thr
            930                 935                 940

Pro Phe Thr Asp Glu Glu Leu Ala Glu Phe Val Asn Arg Gln Leu Val
945                 950                 955                 960

Glu Thr Arg Gln Gly Thr Lys Ala Ile Ile Ser Leu Ile Asn Gln Cys
            965                 970                 975

Phe Pro Asp Ser Glu Val Val Tyr Val Lys Ala Gly Asn Thr Ser Asp
            980                 985                 990

Phe Arg Gln Arg Phe Asp Ile Pro Lys Ser Arg Asp Leu Asn Asn Tyr
            995                 1000                1005

His His Ala Val Asp Ala Tyr Leu Asn Ile Val Gly Asn Val
    1010                1015                1020

Tyr Asp Thr Lys Phe Thr Lys Asn Pro Ile Asn Phe Ile Lys Lys
    1025                1030                1035

Met Arg Lys Ser Gly Asn Leu His Ser Tyr Ser Leu Arg Arg Met
    1040                1045                1050

Tyr Asp Phe Asn Val Gln Arg Gly Asp Gln Thr Ala Trp Val Ala
    1055                1060                1065

Glu Asn Asp Thr Thr Leu Lys Thr Val Lys Thr Ala Phe Lys
    1070                1075                1080

Thr Ser Pro Met Val Thr Lys Arg Thr Tyr Glu Arg Lys Gly Gly
    1085                1090                1095

Leu Ala Asp Ser Val Leu Ile Ala Ala Lys Lys Ala Lys Pro Gly
    1100                1105                1110

Val His Leu Pro Val Lys Thr Ser Asp Ser Arg Phe Ala Asn Gln
    1115                1120                1125

Val Ser Thr Tyr Gly Gly Tyr Asp Asn Val Lys Gly Ser His Phe
    1130                1135                1140

Phe Leu Val Glu His Gln Gln Lys Lys Lys Thr Ile Arg Ser Ile
    1145                1150                1155

Glu Asn Val Pro Ile His Leu Lys Glu Lys Leu Lys Thr Lys Glu
    1160                1165                1170

Glu Leu Glu His Tyr Cys Ala Gln Val Leu Gly Met Val Gln Pro
    1175                1180                1185

Asp Val Arg Leu Thr Arg Ile Pro Met Tyr Ser Leu Leu Leu Ile
    1190                1195                1200

Asp Gly Tyr Tyr Tyr Leu Thr Gly Arg Thr Gly Gly Asn Leu
    1205                1210                1215

Ser Leu Ser Asn Ala Val Glu Leu Cys Leu Pro Ala Lys Glu Gln
    1220                1225                1230

Ala His Ile Arg Met Ile Ser Lys Ile Ala Gly Gly Arg Ser Thr
    1235                1240                1245

Asp Ala Leu Ser Ala Glu Ala Lys Asp Asp Phe Arg Lys Lys Asn
    1250                1255                1260

Leu Arg Leu Tyr Asp Glu Leu Ala Glu Lys His Arg Ser Thr Ile
    1265                1270                1275
```

```
Phe Ser Lys Arg Lys Asn Pro Ile Gly Pro Lys Leu Leu Lys Tyr
    1280            1285            1290

Arg Glu Ala Phe Val Lys Gln Thr Ile Glu Asn Gln Cys Lys Val
    1295            1300            1305

Ile Leu Gln Ile Leu Lys Leu Thr Ser Thr Asn Cys Lys Thr Ser
    1310            1315            1320

Ala Asp Leu Lys Leu Ile Gly Gly Ser Gly Gln Glu Gly Val Met
    1325            1330            1335

Ser Ile Ser Lys Leu Leu Arg Ala Glu Lys Tyr Ala Glu Phe Tyr
    1340            1345            1350

Leu Ile Cys Gln Ser Pro Ser Gly Ile Tyr Glu Thr Arg Lys Asn
    1355            1360            1365

Leu Leu Thr Ile
    1370

<210> SEQ ID NO 2
<211> LENGTH: 294
<212> TYPE: PRT
<213> ORGANISM: Faecalibaculum rodentium

<400> SEQUENCE: 2

Met Thr Trp Arg Thr Ile Thr Ile Ser Ser His Ser Lys Leu Asp Tyr
1               5                   10                  15

Gln Met Gly Tyr Leu Val Val Arg Gly Glu Ser Ile Lys Arg Ile His
                20                  25                  30

Leu Ser Glu Ile Ser Val Leu Ile Ile Glu Asn Thr Ala Val Ser Leu
            35                  40                  45

Thr Ala Tyr Leu Val Ser Glu Leu Val Lys Asn Lys Ile Lys Leu Leu
        50                  55                  60

Phe Cys Asp Glu Lys Arg Ser Pro Leu Ala Glu Val Ser Glu Leu Tyr
65                  70                  75                  80

Gly Gly His Asp Ser Ser Asp Met Val Arg Lys Gln Ile Glu Ile Pro
                85                  90                  95

Gln Glu Arg Lys Asp Ile Ala Trp Gln Ser Ile Ile Met Ser Lys Ile
                100                 105                 110

Ser Asn Gln Phe Ala Val Leu His Asn Phe Asp Cys Pro Asn Gln Glu
            115                 120                 125

Leu Leu Leu Gln Tyr Ile Asn Glu Val Leu Pro Gly Asp Val Thr Asn
        130                 135                 140

Arg Glu Gly His Ala Ala Lys Val Tyr Phe Asn Ser Leu Phe Gly Lys
145                 150                 155                 160

Ser Phe Tyr Arg Ala Ser Glu Cys Ala Leu Asn Ala Ala Leu Asn Tyr
                165                 170                 175

Gly Tyr Ser Val Leu Leu Ser Ala Val Ser Arg Glu Ile Ala Gly Tyr
            180                 185                 190

Gly Phe Leu Thr Gln Leu Gly Ile Phe His Asp Asn Cys Asp Asn Lys
        195                 200                 205

Tyr Asn Leu Ser Cys Asp Leu Met Glu Pro Phe Arg Pro Val Val Asp
        210                 215                 220

Tyr Leu Val Lys Ser Asn Ile Val Glu Val Phe Glu Lys Glu Gln Lys
225                 230                 235                 240

Gln Lys Ile Leu Gln Leu Leu Gln Phe Lys Ile Gln Ile Asn Asp Arg
                245                 250                 255

Gln Glu Thr Val Gln Asn Ala Ile Ser Ile Phe Val His Ser Val Leu
            260                 265                 270
```

Asp Tyr Leu Leu Asp Pro Ser Val Tyr Ile Lys Val Pro Arg Ile Asp
            275                 280                 285

Phe Thr Lys Asn Val Val
            290

<210> SEQ ID NO 3
<211> LENGTH: 68
<212> TYPE: PRT
<213> ORGANISM: Faecalibaculum rodentium

<400> SEQUENCE: 3

Met Met Gln Glu Ser Val Tyr Cys Lys Leu Thr Thr Asn Gln Ser Ser
1               5                   10                  15

Ala Glu Thr Val Leu Lys Met Val Arg Ala Asn Lys Pro Pro Glu Gly
            20                  25                  30

Leu Ile Gln Thr Leu Ile Ile Thr Glu Lys Gln Phe Ser Lys Met Asp
        35                  40                  45

Phe Ile Leu Gly Gln Pro Asn Ser Asp Val Val Ala Thr Asp Glu Ser
    50                  55                  60

Val Leu Asp Leu
65

<210> SEQ ID NO 4
<211> LENGTH: 223
<212> TYPE: PRT
<213> ORGANISM: Faecalibaculum rodentium

<400> SEQUENCE: 4

Met Arg Leu Leu Ile Asp Arg Leu Leu Leu Ser Ala Glu Leu Asn Ile
1               5                   10                  15

Asp Lys Ala Thr Thr Ile Ile Ile Glu Asn Pro Lys Ala Phe Arg Met
            20                  25                  30

Val Ile Lys Asp Leu Ile Glu Gln Glu Asn Gly Gln Gly Gly Leu Leu
        35                  40                  45

Arg Ile Val Glu Gly Asp Lys Glu Leu Cys Leu Ser Lys Ser Ala Ile
    50                  55                  60

Leu Val Leu Asn Pro Tyr Leu Ala Asp Leu Asn Cys Arg Lys Phe Leu
65                  70                  75                  80

Gln Leu Ala Tyr Ser Glu Leu Gln Ala Met Thr Gly Glu Phe Leu Glu
                85                  90                  95

Asp Gln Ala Val Val Leu Ser Ala Met Thr Gly Tyr Leu Ser Lys Ile
            100                 105                 110

Cys Asp Gln Ser Arg Phe Asp Phe Leu Glu Phe Ser Ala Ile Pro Asp
        115                 120                 125

Trp Ala Ser Val Phe Lys Ala Trp Gly Leu Arg Phe Glu Gln Ala Ile
    130                 135                 140

Pro Gly Leu Leu Pro Ser Leu Ile Gln Tyr Leu Gln Leu Ala Ala Thr
145                 150                 155                 160

Phe Pro Gln Phe Lys Leu Ile Ile Phe Ile Asn Leu Lys Gln Tyr Leu
                165                 170                 175

Leu Pro Glu Glu Gln Phe Glu Leu Phe Lys Met Ala Glu Tyr Leu Gln
            180                 185                 190

Leu Lys Val Leu Leu Val Glu Ser Ala Gln Asn Tyr Lys Ser Asp Arg
        195                 200                 205

Glu Asp Leu Ile Ile Ile Asp Lys Asp Leu Cys Glu Ile Gln Ser
    210                 215                 220

<210> SEQ ID NO 5
<211> LENGTH: 20
<212> TYPE: RNA
<213> ORGANISM: Faecalibaculum rodentium

<400> SEQUENCE: 5 guugagugu cuuguuaauu                                             20

<210> SEQ ID NO 6
<211> LENGTH: 36
<212> TYPE: DNA
<213> ORGANISM: Faecalibaculum rodentium

<400> SEQUENCE: 6
gtttgagtgt cttgttaatt cggaagtatt tcaaac                          36

<210> SEQ ID NO 7
<211> LENGTH: 216
<212> TYPE: DNA
<213> ORGANISM: Faecalibaculum rodentium

<400> SEQUENCE: 7
gtttgagtgt cttgttaatt cgggagtagc tctctcgttt gagtgtcttg ttaattcgga    60
agtaagctca acttttgagt gtcttgttaa ttcggaagta tctcaaacgt ttgagtgtct   120
tgttaattca gaagtatttc aaacgtttga gtgtcttgtt aattcggaag tattccaaac   180
gtttgagtgt cttgttaatt cggaagtatt tcaaac                            216

<210> SEQ ID NO 8
<211> LENGTH: 71
<212> TYPE: RNA
<213> ORGANISM: Faecalibaculum rodentium

<400> SEQUENCE: 8
aauuaacaag augaguucaa aucaggcucc uagagagauc cgaacuuacc uucauggcgg    60
gcauugugcc c                                                        71

<210> SEQ ID NO 9
<211> LENGTH: 95
<212> TYPE: RNA
<213> ORGANISM: Artificial sequence
<220> FEATURE:
<223> OTHER INFORMATION: synthetic

<400> SEQUENCE: 9
guuugagugu cuuguuaauu gaaaaauuaa caagaugagu ucaaaucagg cuccuagaga    60
gauccgaacu uaccuucaug gcgggcauug ugccc                              95

<210> SEQ ID NO 10
<211> LENGTH: 91
<212> TYPE: RNA
<213> ORGANISM: Artificial sequence
<220> FEATURE:
<223> OTHER INFORMATION: synthetic

<400> SEQUENCE: 10
guuugagugu cuuguuaaga aauuaacaag augaguucaa aucaggcucc uagagagauc    60
cgaacuuacc uucauggcgg gcauugugcc c                                  91

<210> SEQ ID NO 11

```
<211> LENGTH: 89
<212> TYPE: RNA
<213> ORGANISM: Artificial sequence
<220> FEATURE:
<223> OTHER INFORMATION: synthetic

<400> SEQUENCE: 11
guuugagugu cuuguuagaa auaacaagau gaguucaaau caggcuccua gagagauccg    60
aacuuaccuu cauggcgggc auugugccc                                     89

<210> SEQ ID NO 12
<211> LENGTH: 87
<212> TYPE: RNA
<213> ORGANISM: Artificial sequence
<220> FEATURE:
<223> OTHER INFORMATION: synthetic

<400> SEQUENCE: 12
guuugagugu cuuguugaaa acaagauga guucaaauca ggcuccuaga gagauccgaa    60
cuuaccuuca uggcgggcau ugugccc                                       87

<210> SEQ ID NO 13
<211> LENGTH: 85
<212> TYPE: RNA
<213> ORGANISM: Artificial sequence
<220> FEATURE:
<223> OTHER INFORMATION: synthetic

<400> SEQUENCE: 13
guuugagugu cuugugaaaa caagaugagu ucaaaucagg cuccuagaga gauccgaacu   60
uaccuucaug gcgggcauug ugccc                                         85

<210> SEQ ID NO 14
<211> LENGTH: 83
<212> TYPE: RNA
<213> ORGANISM: Artificial sequence
<220> FEATURE:
<223> OTHER INFORMATION: synthetic

<400> SEQUENCE: 14
guuugagugu cuuggaaaca agaugaguuc aaaucaggcu ccuagagaga uccgaacuua   60
ccuucauggc gggcauugug ccc                                           83

<210> SEQ ID NO 15
<211> LENGTH: 79
<212> TYPE: RNA
<213> ORGANISM: Artificial sequence
<220> FEATURE:
<223> OTHER INFORMATION: synthetic

<400> SEQUENCE: 15
guuugagugu cugaaaagau gaguucaaau caggcuccua gagagauccg aacuuaccuu   60
cauggcgggc auugugccc                                                79

<210> SEQ ID NO 16
<211> LENGTH: 75
<212> TYPE: RNA
<213> ORGANISM: Artificial sequence
<220> FEATURE:
<223> OTHER INFORMATION: synthetic

<400> SEQUENCE: 16
guuugagugu gaaaaugagu ucaaaucagg cuccuagaga gauccgaacu uaccuucaug   60
```
gcgggcauug ugccc                                                           75

<210> SEQ ID NO 17
<211> LENGTH: 71
<212> TYPE: RNA
<213> ORGANISM: Artificial sequence
<220> FEATURE:
<223> OTHER INFORMATION: synthetic

<400> SEQUENCE: 17
guuugaguga aagaguucaa aucaggcucc uagagagauc cgaacuuacc uucauggcgg          60
gcauugugcc c                                                              71

<210> SEQ ID NO 18
<211> LENGTH: 69
<212> TYPE: DNA
<213> ORGANISM: Artificial Sequence
<220> FEATURE:
<223> OTHER INFORMATION: Synthetic

<400> SEQUENCE: 18
ctacctgcat accgttatta acatatgaca actcaattaa acgccacatc catcggcgct          60
ttggtcggc                                                                 69

<210> SEQ ID NO 19
<211> LENGTH: 62
<212> TYPE: DNA
<213> ORGANISM: Artificial Sequence
<220> FEATURE:
<223> OTHER INFORMATION: Synthetic

<400> SEQUENCE: 19
atgttaccac tggattgagg ataccgttat taacatatga caactcaatt aaactctggt         60
ac                                                                        62

<210> SEQ ID NO 20
<211> LENGTH: 69
<212> TYPE: DNA
<213> ORGANISM: Artificial Sequence
<220> FEATURE:
<223> OTHER INFORMATION: Synthetic

<400> SEQUENCE: 20
tcagtttata tgagttacaa cgaacaccgt ttaattgagt tgtcatatgt taataacggt         60
attcaggta                                                                 69

<210> SEQ ID NO 21
<211> LENGTH: 69
<212> TYPE: DNA
<213> ORGANISM: Artificial Sequence
<220> FEATURE:
<223> OTHER INFORMATION: Synthetic

<400> SEQUENCE: 21
ctacctacat accgttatta acatatgaca actcaattaa acgtcagcac ctgggacccc         60
gccaccgtg                                                                 69

<210> SEQ ID NO 22
<211> LENGTH: 34
<212> TYPE: DNA
<213> ORGANISM: Artificial Sequence
<220> FEATURE:

```
<223> OTHER INFORMATION: Synthetic

<400> SEQUENCE: 22
gtttaattga gttgtcatat gttaataacg gtat                                        34

<210> SEQ ID NO 23
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(26)
<223> OTHER INFORMATION: n is a, c, g, or t;r is a or g;w is a or t.

<400> SEQUENCE: 23
tgttaccact ggattgaggt cnnrwr                                                 26

<210> SEQ ID NO 24
<211> LENGTH: 26
<212> TYPE: DNA
<213> ORGANISM: Artificial Sequence
<220> FEATURE:
<223> OTHER INFORMATION: Synthetic

<400> SEQUENCE: 24
tgttaccact ggattgaggt ctggta                                                 26

<210> SEQ ID NO 25
<211> LENGTH: 26
<212> TYPE: DNA
<213> ORGANISM: Artificial Sequence
<220> FEATURE:
<223> OTHER INFORMATION: Synthetic

<400> SEQUENCE: 25
aagaaccact ggattgaggt ctggct                                                 26

<210> SEQ ID NO 26
<211> LENGTH: 26
<212> TYPE: DNA
<213> ORGANISM: Artificial Sequence
<220> FEATURE:
<223> OTHER INFORMATION: Synthetic

<400> SEQUENCE: 26
gggaaccact ggattaaggt ccagat                                                 26

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27
agttaccaat ggattgagat ggggag                                                 26

<210> SEQ ID NO 28
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (22)..(26)
<223> OTHER INFORMATION: n is a, c, g, or t;r is a or g;w is a or t.

<400> SEQUENCE: 28
aaaaaggaag gagttctttg tnnrwr                                          26

<210> SEQ ID NO 29
<211> LENGTH: 26
<212> TYPE: DNA
<213> ORGANISM: Artificial Sequence
<220> FEATURE:
<223> OTHER INFORMATION: Synthetic

<400> SEQUENCE: 29
aaaaaggaag gagttctttg taggta                                          26

<210> SEQ ID NO 30
<211> LENGTH: 26
<212> TYPE: DNA
<213> ORGANISM: Artificial Sequence
<220> FEATURE:
<223> OTHER INFORMATION: Synthetic

<400> SEQUENCE: 30
taaaaggaag gtgttctttg tggggt                                          26

<210> SEQ ID NO 31
<211> LENGTH: 26
<212> TYPE: DNA
<213> ORGANISM: Artificial Sequence
<220> FEATURE:
<223> OTHER INFORMATION: Synthetic

<400> SEQUENCE: 31
gaaaaggaag gtgctctttg tgggtg                                          26

<210> SEQ ID NO 32
<211> LENGTH: 26
<212> TYPE: DNA
<213> ORGANISM: Artificial Sequence
<220> FEATURE:
<223> OTHER INFORMATION: Synthetic

<400> SEQUENCE: 32
ggaaaaggtg gaattctttg ttggta                                          26

<210> SEQ ID NO 33
<211> LENGTH: 17
<212> TYPE: DNA
<213> ORGANISM: Artificial Sequence
<220> FEATURE:
<223> OTHER INFORMATION: Synthetic

<400> SEQUENCE: 33
cgaacacctc aggtaat                                                    17
```

TYPE II CRISPR/CAS9 GENOME EDITING SYSTEM AND THE APPLICATION THEREOF

SUBMISSION OF SEQUENCE LISTING ON ASCII TEXT FILE

The substitute sequence listing is submitted to replace the previously submitted sequence listing as an ASCII formatted text filed via EFS-Web, with a file name of "Substitute_Sequence_Listing.txt", a creation date of Dec. 19, 2023, and a size of 23 KB. The substitute sequence Listing filed via EFS-Web is part of the specification and is incorporated in its entirety by reference herein.

TECHNICAL FIELD

The disclosure relates to a Type II CRISPR/Cas9 genome editing system derived from *Faecalibaculum rodentium*, belonging to the technical field of genome editing.

BACKGROUND ART

Gene editing technology makes it possible to modify DNA sequence localization points. For example, the first generation of genome editing tools zinc finger nucleases, (ZFNs), the second generation of genome editing tools such as transcription activator-like effector nucleases (TALENs) can all be used to transform targeted genomes. However, these methods are difficult to design, not easy to manufacture, expensive and not universal.

The CRISPR (Clustered Regularly Interspaced Short Palindromic Repeat)/Cas (CRISPR-associated protein) system is the innate immune system derived from archaea and bacteria, serving as the third-generation genome editing tool. Different from that previous genome editing tools (protein-DNA recognition), the method utilizes the principle of nucleic acid base complementary pair to identify the target DNA sequence and guide the Cas effector protein to carry out site-specific cleaving, and has the advantages of high applicability, simple design, low cost and high efficiency. Cas protein contains a variety of different effector domains, which play roles in different activities such as nucleic acid recognition, stabilization of complex structures, and hydrolysis of DNA phosphodiester bonds. Among them, the Type II CRISPR/Cas9 system derived from *streptococcus pyogene* Cas (SpCas9) has become the most widely used CRISPR/Cas system due to its high cleavage efficiency. This system identifies and cleaves the Protospacer Adjacent Motif (PAM) sequence, i.e. "NGG" on the targeted polynucleotide, leaving a flat-ended overhang, and affecting genome editing.

In large and diverse metagenomes harboring uncultured or even undiscovered microorganisms, there may be a large number of undiscovered CRISPR/Cas9 systems whose activities in prokaryotes and eukaryotes, as well as in vitro environments, need to be confirmed.

In 2015, Dr. Byoung-Chan Kim's team isolated a new anaerobic strain ALO17 from the feces of laboratory mice C57BL/6J, and analyzed the phylogenetic relationship of the strain with the 16SrRNA gene sequence of prokaryote, and found that the strain is closely related to Holdemanellabiformis DSM 3989T, Faecalicoccuspleomorphus ATCC 29734T, Faecalitaleacylindroides ATCC 27803T, and Allobaculumstercoricanis DSM 13633T (sequence homologies are 87.4%, 87.3%, 86.9% and 86.9%, respectively). On the basis of multiple taxonomic evidences, this species is considered to be a new genus of the Erysipelothricaceae family, and named as *Faecalibaculum rodentium* Gen.nov., sp. nov. In the past five years, scientists in various countries around the world have carried out research on this strain in two fields, i.e., intestinal microbial environment and high-fat diet, and intestinal microbial environment and tumorigenesis. However, it has not been reported in the field of genome editing.

SUMMARY OF THE DISCLOSURE

The purpose of the disclosure is to overcome the defects of the prior art and provide a Type II CRISPR/Cas9 genome editing system derived from *Faecalibaculum rodentium*, wherein the genome editing system has new physical and chemical properties and can identify a plurality of different PAM (protospacer adjacent motif) sequences, including NGTA and NNTA (N is A, C, G, or T).

In order to achieve the purpose, the technical solution adopted by the disclosure is as follows.

A Type II CRISPR/Cas9 genome editing system, characterized in that, the system comprises a Cas9 protein, helper proteins, a crRNA(CRISPR RNA) and a tracrRNA (transactivated CRISPR RNA) in the functional form of an RNP complex (ribonucleoprotein complex) of the Cas9 protein and a guide RNA formed by hybridizing the crRNA with the tracrRNA;

wherein the Cas9 protein is a DNA endonuclease, and the Cas9 protein has an amino acid sequence as shown in SEQ ID NO: 1, or an amino acid sequence with at least 80%, 85%, 90%, 95%, 98%, or 99% homology to the amino acid sequence as shown in SEQ ID NO: 1.

Preferably, the Type II CRISPR/Cas9 genome editing system is derived from *Faecalibaculum rodentium*.

The Cas9 protein cleaves a double-stranded DNA complementary to a crRNA upstream of a PAM sequence by a nuclease domain, wherein the nuclease domain is selected from a HNH-like nuclease domain, a RuvC-like nuclease domain, or a combination thereof.

In some embodiments, the term "ribonucleoprotein complex" is preferably referred to the "FrCas9 protein complex" according to the disclosure.

The mutations at several key amino acid sites of the specific Cas9 protein are explained in details as follows. The mutation of E to A at 796 position amino acid will result in nickase nuclease. The mutation of N to A at 902 position amino acid will result in nickase nuclease. The mutation of H to A at 1010 position amino acid will result in nickase nuclease. The mutation of D to A at 1013 position amino acid will result in nickase nuclease.

The simultaneous mutation of E to A at 796 position amino acid and D to A at 1013 position amino acid will result in a Cas9 nuclease that is non-cleaving but retains binding (i.e., dead Cas9).

The helper proteins comprise a Cas1 helper protein, a Cas2 helper protein and a Csn2 helper protein;

wherein the Cas1 helper protein has an amino acid sequence as shown in SEQ ID NO: 2, or an amino acid sequence with at least 80%, 85%, 90%, 95%, 98%, or 99% homology to the amino acid sequence as shown in SEQ ID NO: 2;

wherein the Cas2 helper protein has an amino acid sequence as shown in SEQ ID NO: 3, or an amino acid sequence with at least 80%, 85%, 90%, 95%, 98%, or 99% homology to the amino acid sequence as shown in SEQ ID NO: 3;

wherein the Csn2 helper protein has an amino acid sequence as shown in SEQ ID NO: 4, or an amino acid sequence with at least 80%, 85%, 90%, 95%, 98%, or 99% homology to the amino acid sequence as shown in SEQ ID NO: 4.

The CRISPR RNA is generated by transcription of a CRISPR Array, and has an RNA sequence as shown in SEQ ID NO: 5, or an RNA sequence with at least 80%, 85%, 90%, 95%, 98%, or 99% homology to the nucleic acid sequence as shown in SEQ ID NO: 5; wherein the CRISPR Array comprises a direct repeat sequence and a spacer sequence, wherein the direct repeat sequence has a nucleic acid sequence as shown in SEQ ID NO: 6, or a nucleic acid sequence with at least 80%, 85%, 90%, 95%, 98%, or 99% homology to the nucleic acid sequence as shown in SEQ ID NO: 6; and wherein the spacer sequence has a nucleic acid sequence as shown in SEQ ID NO: 7, or a nucleic acid sequence with at least 80%, 85%, 90%, 95%, 98%, or 99% homology to the nucleic acid sequence as shown in SEQ ID NO: 7.

The trans-activated CRISPR RNA comprises a sequence complementary to a direct repeat sequence of the CRISPR RNA, and the trans-activated CRISPR RNA has a nucleic acid sequence as shown in SEQ ID NO: 8, or a nucleic acid sequence with at least 70%, 80%, 85%, 90%, 95%, 98%, or 99% to the nucleic acid sequence as shown in SEQ ID NO: 8.

The guide RNA formed by hybridizing the crRNA with the tracrRNA has a scaffold composed of a sequence of 7 to 24 nts of a crRNA direct repeat sequence and a tracrRNA sequence; preferably the two parts are fused by a "GAAA", "TGAA", or "AAAC" linker to form an sgRNA scaffold; preferably, an sgRNA scaffold formed by fusion of the crRNA direct repeat sequence of 20 nts and a full length sequence of the tracrRNA by "GAAA" is as shown in SEQ ID NO: 9, and on this basis, preferably, a highly efficient variant of an sgRNA scaffold is an sgRNA scaffold formed by fusion of the first 18 to 14 nts of the crRNA direct repeat sequence and the last 69 to 65 nts of the tracrRNA by a linker sequence (for example, "GAAA"), preferably selected from the following five scaffolds:
(1) an sgRNA scaffold with a length of 91 nts, which comprises 18 nts direct repeat sequence and 69 nts tracrRNA, as shown in SEQ ID NO: 10;
(2) an sgRNA scaffold with a length of 89 nts, which comprises 17 nts direct repeat sequence and 68 nts tracrRNA, as shown in SEQ ID NO: 11;
(3) an sgRNA scaffold with a length of 87 nts, which comprises 16 nts direct repeat sequence and 67 nts tracrRNA, as shown in SEQ ID NO: 12;
(4) an sgRNA scaffold with a length of 85 nts, which comprises 15 nts direct repeat sequence and 66 nts tracrRNA, as shown in SEQ ID NO: 13;
(5) an sgRNA scaffold with a length of 83 nts, which comprises 14 nts direct repeat sequence and 65 nts tracrRNA, as shown in SEQ ID NO: 14;
optionally, the sgRNA scaffold has a nucleic acid sequence with at least 70%, 80%, 85%, 90%, 95%, 98%, or 99% homology to any of SEQ ID NOs: 9 to 14.

The Type II CRISPR/Cas9 genome editing system, derived from *Faecalibaculum rodentium*, binds or cleaves a specific DNA in a biological process (such as genome editing process), by complementary pairing recognition of the guide RNA and a target of the specific DNA, and wherein a length of a paired binding part of the guide RNA and the target of the specific DNA ranges from 14 to 30 bps (preferably 20 to 23 bps); wherein the specific DNA is a DNA of prokaryote or eukaryote.

The length of the paired binding part of the guide RNA and the target of the specific DNA is 21 bps, 22 bps or 23 bps, and wherein the RNP complex is highly sensitive to base mismatch of 14 bps close to a protospacer adjacent motif and the 14 bps is a seed region.

The protospacer adjacent motif required for a function of binding or cleaving DNA is 5'-NNTA-3' downstream of the guide RNA/sgRNA recognition sequence.

In some embodiments, the disclosure further provides a method for editing or binding DNA, comprising:
processing the DNA using the Type II CRISPR/Cas9 genome editing system above.

Preferably, the DNA is prokaryotic or eukaryotic DNA. Preferably, the abovementioned Type II CRISPR/Cas9 genome editing system is derived from *Faecalibaculum rodentium*.

In some embodiments, the disclosure provides a method for CRISPR activation, comprising:
proceeding the CRISPR activation using the Type II CRISPR/Cas9 genome editing system above.

In some embodiments, the disclosure further provides a method for CRISPR interference, comprising:
proceeding the CRISPR interference using the Type II CRISPR/Cas9 genome editing system above.

In some embodiments, the disclosure provides a method for preparing a nickase, comprising:
preparing the nickase using the Type II CRISPR/Cas9 genome editing system above.

Preferably, the nickase is prepared in a prokaryote or a eukaryote.

In some embodiments, the disclosure further provides a method for preparing a dead Cas9, comprising:
preparing the dead Cas9 using the Type II CRISPR/Cas9 genome editing system above.

Preferably, the dead Cas9 is prepared in a prokaryote or a eukaryote.

In some embodiments, the disclosure provides a genome editing tool, comprising:
the Type II CRISPR/Cas9 genome editing system above, wherein the genome editing tool is a base editor.

In some embodiments, the disclosure provides a genome editing tool, comprising:
the Type II CRISPR/Cas9 genome editing system above, wherein the genome editing tool is a prime editor.

Compared with the prior art, the disclosure has the beneficial effects as follows:
(1) According to the disclosure, through bioinformatics analysis, a Type II CRSIPR/Cas9 genome editing system in *Faecalibaculum rodentium* is found, and the genome editing system is applied to editing prokaryotic or eukaryotic genes and provides a new option in the genome editing toolbox.
(2) The disclosure provides a Type II CRISPR/Cas9 genome editing system derived from *Faecalibaculum rodentium*, which has new physical and chemical properties and can identify a plurality of different PAM sequences, wherein the specific sequence of PAM recognized by the genome editing system is 5'-NNTA-3' downstream of the guide RNA/sgRNA recognition sequence.
(3) The disclosure provides a Type II CRISPR/Cas9 genome editing system derived from *Faecalibaculum rodentium*, which has high cleavage efficiency on the same DNA site compared with the most common SpCas9, while the off-target is lower than the most common SpCas9, such that it is a safer and more effective genome editing tool.

(4) The disclosure provides a Type II CRISPR/Cas9 genome editing system derived from *Faecalibaculum rodentium*, wherein the PAM recognized at the genome editing system level has palindrome characteristics, and targets therefore are distributed "back-to-back" on a genome, which has a higher density than SpCas9.

(5) The disclosure provides a Type II CRISPR/Cas9 genome editing system derived from *Faecalibaculum rodentium*, which has high flexibility and can be modified into a base editor and a prime editor, and is a genome editing tool capable of being widely applied to different scenarios.

BRIEF DESCRIPTION OF THE DRAWINGS

FIG. 3A shows the full length 95 nts gRNA. The sequence of 95 nts sgRNA is designated SEQ ID NO:9. FIG. 3B shows an sgRNA scaffold with a length of 91 nts, which comprises 18 nts direct repeat sequence and 69 nts tracrRNA. The sequence of 91 nts sgRNA is designated SEQ ID NO:10. FIG. 3C shows an sgRNA scaffold with a length of 89 nts, which comprises 17 nts direct repeat sequence and 68 nts tracrRNA. The sequence of 89 nts sgRNA is designated SEQ ID NO:11. FIG. 3D shows an sgRNA scaffold with a length of 87 nts, which comprises 16 nts direct repeat sequence and 67 nts tracrRNA. The sequence of 87 nts sgRNA is designated SEQ ID NO:12. FIG. 3E shows an sgRNA scaffold with a length of 85 nts, which comprises 15 nts direct repeat sequence and 66 nts tracrRNA. The sequence of 85 nts sgRNA is designated SEQ ID NO:13. FIG. 3F shows an sgRNA scaffold with a length of 83 nts, which comprises 14 nts direct repeat sequence and 65 nts tracrRNA. The sequence of 83 nts sgRNA is designated SEQ ID NO:14.

FIG. 6A is an ODN-PCR gel diagram. FIG. 6B is a Sanger sequence peak. The sequence of FANCF-T4 is designated SEQ ID NO:18; the sequence of DYRK1A-T2 is designated SEQ ID NO:19; the sequence of RNF2-T6 is designated SEQ ID NO:20; the sequence of FANCF-T1 is designated SEQ ID NO:21; and the sequence of ODN tag is designated SEQ ID NO:22.

FIG. 7A is a graph showing the cleavage efficiency of different sgRNA lengths at the HEK293 SITE2-T2 site. FIG. 7B is a graph showing the cleavage efficiency of different sgRNA lengths at the DNMT1-T3 site.

FIG. 9 is a schematic diagram showing the comparison of the target efficiency and off-target of GUIDE-seq in the Type II CRISPR/Cas9 genome editing system of *Faecalibaculum rodentium* according to the disclosure as compared with SpCas9. There are 5 nucleotide sequences from top to bottom of DYRK1A-T2, which are sequence 1 as set forth in SEQ ID NO: 23, sequence 2 as set forth in SEQ ID NO: 24, sequence 3 as set forth in SEQ ID NO: 25, sequence 4 as set forth in SEQ ID NO: 26, and sequence 5 as set forth in SEQ ID NO: 27. There are 5 nucleotide sequences from top to bottom of GRIN2B-T9, which are sequence 1 as set forth in SEQ ID NO: 28, sequence 2 as set forth in SEQ ID NO: 29, sequence 3 as set forth in SEQ ID NO: 30, sequence 4 as set forth in SEQ ID NO: 31, and sequence 5 as set forth in SEQ ID NO: 32.

FIGS. 10A-10E are graphs showing experimental results of the FrCas9-BE base editor; wherein, FIG. 10A is a schematic diagram and results of confirming the form of FrCas9 nickase by ODN breakpoint PCR; FIG. 10B is the editing window for the nFrCas9-BE4 Gram; FIG. 10C is the editing window for nFrCas9-ABE7.10; FIG. 10D is a Venn diagram of pathogenic mutations in the ClinVar database that can be uniquely corrected by the SpCas9 and FrCas9 base editors; FIG. 10E shows the C>T editing efficiency for FrCas9-BE4Gam using 2 "back-to-back" sgRNA simultaneously.

FIG. 11A shows the distribution of 5'-GG-3' (representing SpCas9 PAM) in the GRCh38 human genome; FIG. 11B shows the distribution of 5'-TA-3' (representing FrCas9 PAM) in the GRCh38 human genome.

FIGS. 12A-12C shows the application of FrCas9-specific targeted TATA box in CRISPR interference and CRISPR activation, wherein FIG. 12A is a schematic diagram of the TATA-box of the ABCA1 gene targeted by FrCas9;

FIG. 12B shows CRISPR interference of FrCas9 and SpCas9 by targeting TATA-box, and CRISPR activation of FrCas9 and SpCas9 by targeting TATA-box;

FIG. 12C shows CRISPR activation of FrCas9 and SpCas9 by targeting the TATA-box.

DETAILED DESCRIPTION OF THE DISCLOSURE

In order to better explain the objects, technical solutions and advantages of the disclosure, the disclosure will be further described below with reference to specific embodiments.

Figure 1:
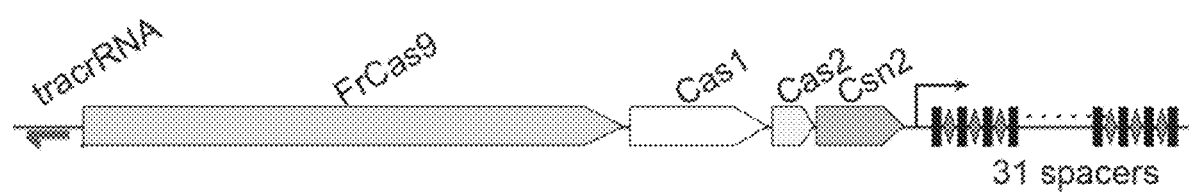
FIG. 1 is a composition diagram of a Type II CRISPR/Cas9 genome editing system of *Faecalibaculum rodentium* according to the disclosure.

A Type II CRISPR/Cas9 genome editing system derived from *Faecalibaculum rodentium* comprises a Cas9 protein, helper proteins, a CRISPR RNA and a trans-activated CRISPR RNA, as shown in FIG. 1. The Cas9 protein is a DNA endonuclease, and the Cas9 protein has an amino acid sequence as shown in SEQ ID NO: 1, or an amino acid sequence with at least 80%, 85%, 90%, 95%, 98%, or 99% homology to the amino acid sequence as shown in SEQ ID NO: 1.

Figure 2:
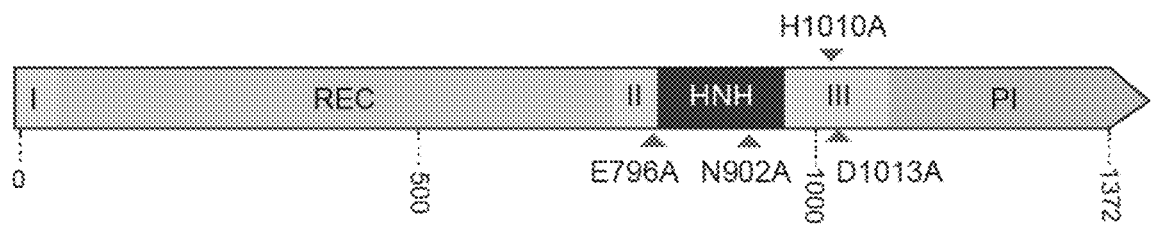
FIG. 2 is a structural diagram of Cas9 protein of the Type II CRISPR/Cas9 genome editing system of *Faecalibaculum rodentium* according to the disclosure.
Figure 3A:
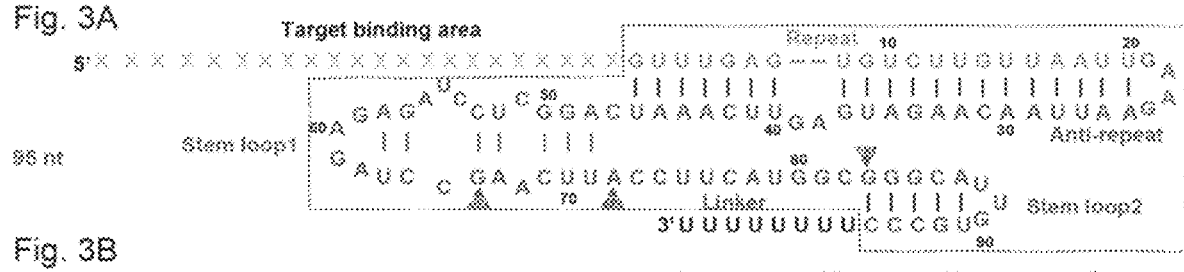
FIGS. 3A-3F show an RNA secondary structure prediction diagram and an optimal sgRNA scaffold diagram of a guide RNA molecule recognized by the Type II CRISPR/Cas9 genome editing system of *Faecalibaculum rodentium* according to the disclosure.
Figure 3B:
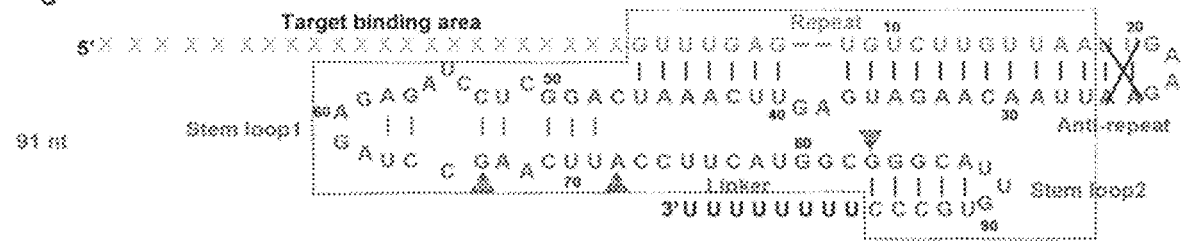
Figure 3C:
Figure 3D:
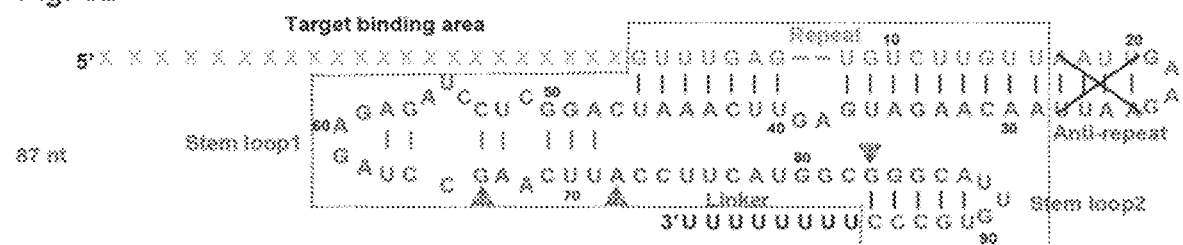
Figure 3E:
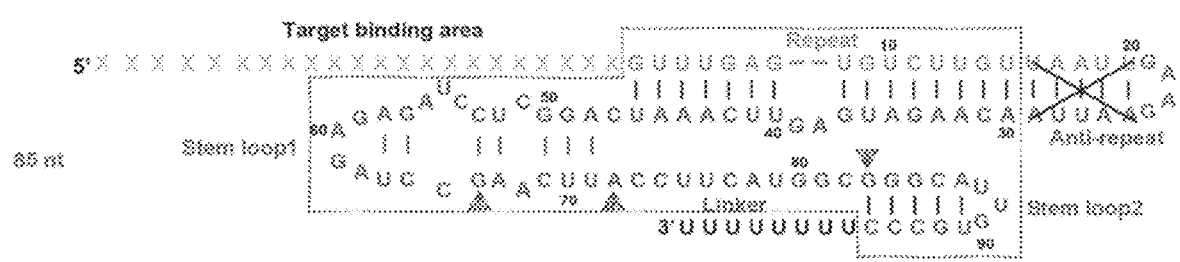
Figure 3F:
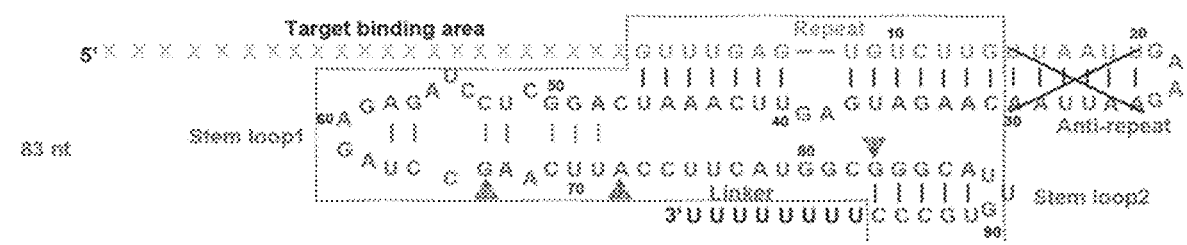

As a preferred embodiment of the Type II CRISPR/Cas9 genome editing system derived from *Faecalibaculum rodentium* according to the disclosure, the Cas9 protein cleaves a double-stranded DNA complementary to crRNA upstream of the PAM sequence by a nuclease domain, as shown in FIG. 2. The nuclease domain is selected from a HNH-like nuclease domain, a RuvC-like nuclease domain, or a combination thereof.

The Cas9 protein (*Faecalibaculum rodentium* Cas9), abbreviated as FrCas9 protein, comprises 1372 amino acids (SEQ ID NO: 1), and is a multi-domain and multifunctional DNA endonuclease. It efficiently cleaves a double-stranded DNA complementary to sgRNA upstream of the PAM by a nuclease domain, for example, cleaving a DNA strand complementary to the sgRNA sequence by a HNH-like nuclease domain, or cleaving a non-complementary strand DNA by a RuvC-like nuclease domain. Among them, The mutation of E to A at 796 position amino acid will result in nickase nuclease. The mutation of N to A at 902 position amino acid will result in nickase nuclease. The mutation of H to A at 1010 position amino acid will result in nickase nuclease. The mutation of D to A at 1013 position amino acid will result in nickase nuclease. The simultaneous mutation of E to A at 796 position amino acid and D to A at 1013 position amino acid will result in a Cas9 nuclease that is non-cleaving but retains binding.

As a preferred embodiment of the Type II CRISPR/Cas9 genome editing system derived from *Faecalibaculum rodentium* according to the disclosure, the helper proteins comprise a Cas1 helper protein, a Cas2 helper protein and a Csn2 helper protein. The Cas1 helper protein has an amino acid sequence as shown in SEQ ID NO: 2, or an amino acid sequence with at least 80%, 85%, 90%, 95%, 98%, or 99% homology to the amino acid sequence as shown in SEQ ID NO: 2. The Cas2 helper protein has an amino acid sequence as shown in SEQ ID NO: 3, or an amino acid sequence with at least 80%, 85%, 90%, 95%, 98%, or 99% homology to the amino acid sequence as shown in SEQ ID NO: 3. The Csn2 helper protein has an amino acid sequence as shown in SEQ ID NO: 4, or an amino acid sequence with at least 80%, 85%, 90%, 95%, 98%, or 99% homology to the amino acid sequence as shown in SEQ ID NO: 4.

The helper proteins Cas1, Cas2 and Csn2 according to the disclosure participate in exogenous gene capture and maturation of crRNA.

As a preferred embodiment of the Type II CRISPR/Cas9 genome editing system derived from *Faecalibaculum rodentium* according to the disclosure, the CRISPR RNA is generated by transcription of a CRISPR Array. The CRISPR RNA has an RNA sequence as shown in SEQ ID NO: 5, or an RNA sequence with at least 80%, 85%, 90%, 95%, 98%, or 99% homology to the nucleic acid sequence as shown in SEQ ID NO: 5. The CRISPR Array comprises a direct repeat sequence and a spacer sequence. The direct repeat sequence is as shown in SEQ ID NO: 6. The spacer sequence is as shown in SEQ ID NO: 7.

The CRISPR RNA(crRNA) according to the disclosure guides the Cas protein to recognize an intruding foreign genome in a base complementary form. When bacteria are exposed to invasion by bacteriophage or virus, a short segment of foreign DNA is integrated as a new spacer between CRISPR repeated spacer sequences in the host chromosome, thereby providing a genetic record of infection. When the body is invaded by a foreign gene again, the CRISPR array transcribes and produces a precursor crRNA (pre-crRNA) with a spacer sequence at the 5' end and a length of 30 bps, which is complementary to the sequence from the foreign invasion gene. The 3' end is a repeat sequence with a length of 36 bps.

As a preferred embodiment of the Type II CRISPR/Cas9 genome editing system derived from *Faecalibaculum rodentium* according to the disclosure, the trans-activated CRISPR RNA comprises a sequence complementary to a direct repeat sequence of the CRISPR RNA as shown in SEQ ID NO: 8.

The trans-activated crRNA(tracrRNA) according to the disclosure is a non-protein encoded RNA, and participates in the maturation of crRNA and the formation of sgRNA. Under the action of the tracrRNA and Cas9 nuclease, the pre-crRNA removes 0 to 16 nts upstream of the spacer sequence and 12 to 29 nts downstream of the repeat sequence to form mature crRNA, and binds the tracrRNA to form a tracrRNA-crRNA complex, which comprises a part recognizing the foreign DNA sequence and has length ranging from 14 to 30 bps. Tetraloop (for example, a "GAAA", "TGAA" or "AAAC" sequence) of four bases may be added between downstream of the crRNA and upstream of the tracrRNA to bind the tracrRNA and the crRNA, in order to form an sgRNA comprising two bulge and three duplex structures upstream, as well as a stem loop structure downstream, which can be further divided into a part that recognizes a foreign DNA sequence and a scaffold part.

The cleavage by the endonuclease can be further optimized by adjusting the length of the part of the sgRNA recognizing the foreign DNA sequence and the length of the tracrRNA. The early experiments of the disclosure prove that, the optimal length of the part of sgRNA recognizing the exogenous DNA sequence is 21 bps, 22 bps or 23 bps (as shown in FIG. 8), and the optimal length of the scaffold part is as follow 5 kinds, as shown in FIGS. 3A-3F and FIGS. 7A-7C: 91 nts (18 nts crRNA direct repeat+69 nts tracrRNA), 89 nts (17 nts crRNA direct repeat+68 nts tracrRNA), 87 nts (16 nts crRNA direct repeat+67 nts tracrRNA), 85 nts (15 nts crRNA direct repeat+66 nts tracrRNA), and 83 nts (14 nts crRNA direct repeat+65 nts tracrRNA).

As a preferred embodiment of the Type II CRISPR/Cas9 genome editing system derived from *Faecalibaculum rodentium* according to the disclosure, the *Faecalibaculum rodentium*-derived Type II CRISPR/Cas9 genome editing system binds or cleaves structures of DNA functions in a genome editing process.

As a preferred embodiment of the Type II CRISPR/Cas9 genome editing system derived from *Faecalibaculum rodentium* according to the disclosure, the DNA is a DNA of prokaryote or eukaryote.

Figure 4:
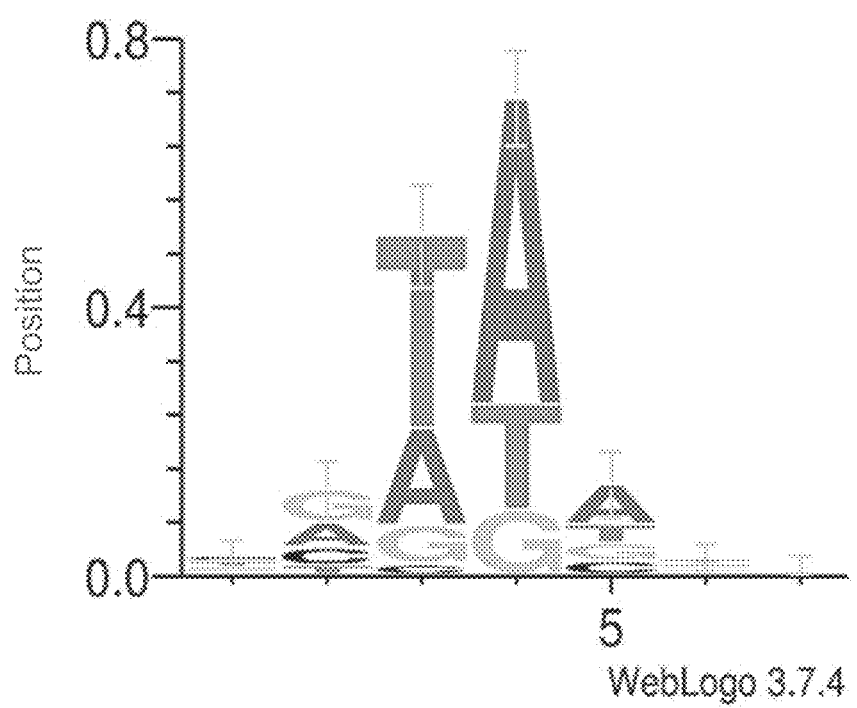
FIG. 4 is a schematic diagram of prokaryotic PAM sequences of the Type II CRISPR/Cas9 genome editing system of *Faecalibaculum rodentium* according to the disclosure.
Figure 5A:
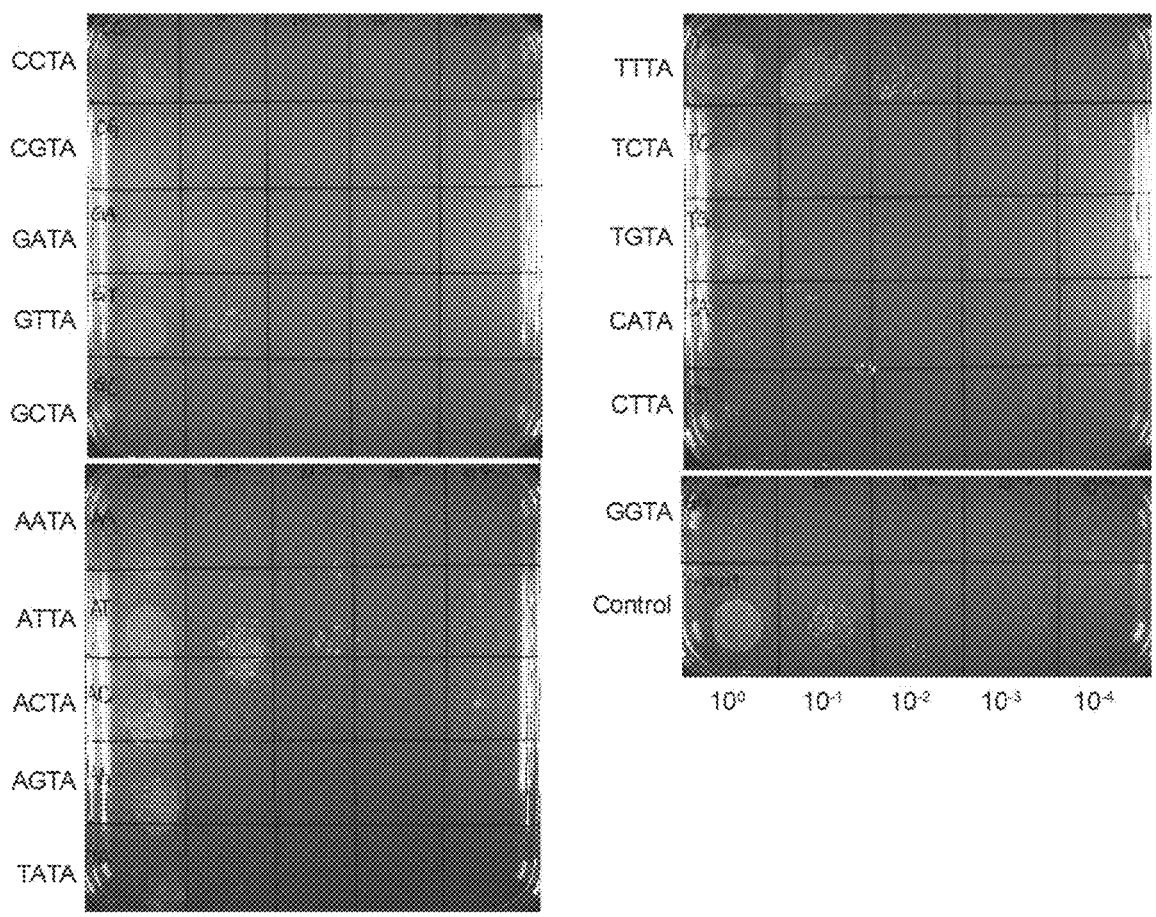
FIGS. 5A-5C show schematic diagrams of prokaryotic interference experiments of the Type II CRISPR/Cas9 genome editing system of *Faecalibaculum rodentium* according to the disclosure.
Figure 5B:
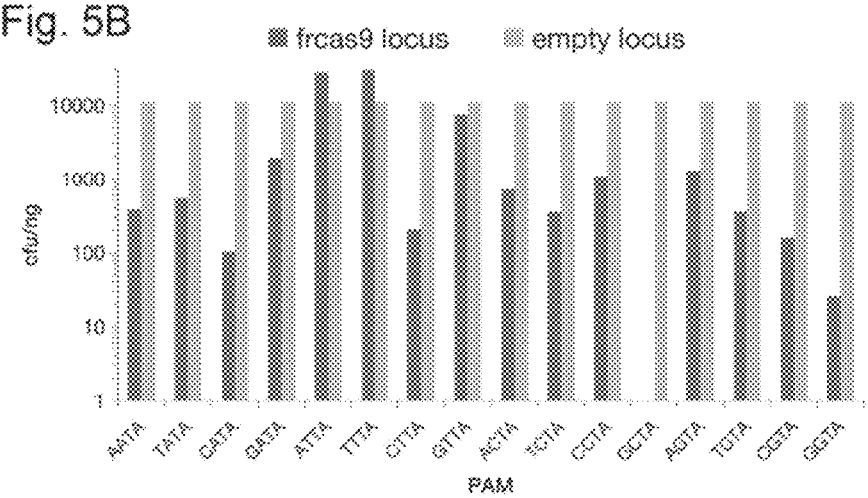
Figure 5C:
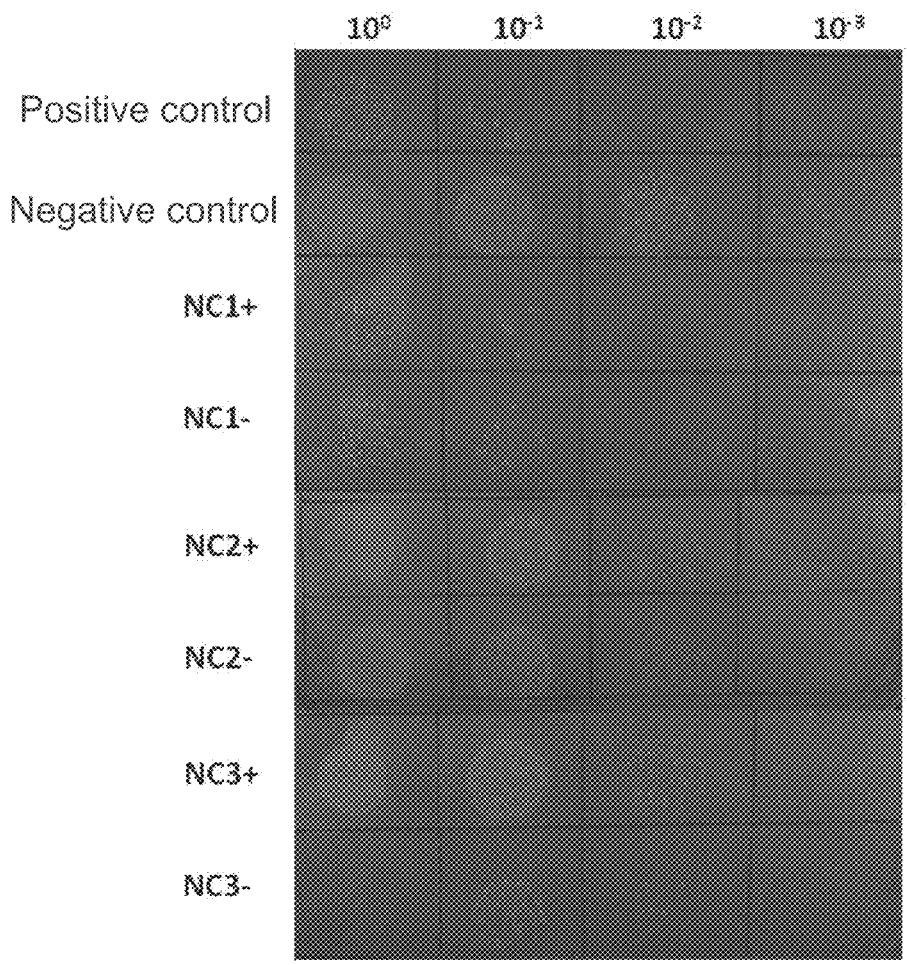
Figure 6A:
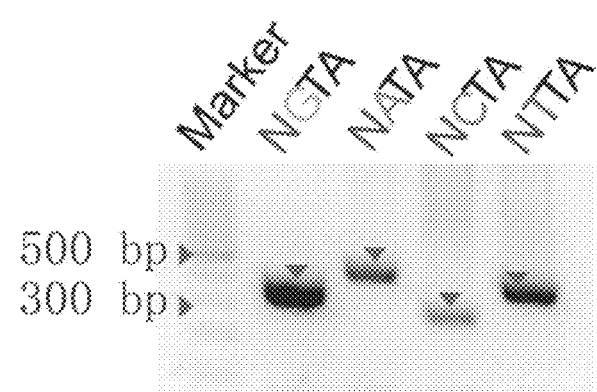
FIGS. 6A-6B show schematic diagrams of eukaryotic cleaving of the Type II CRISPR/Cas9 genome editing system of *Faecalibaculum rodentium* according to the disclosure.
Figure 6B:
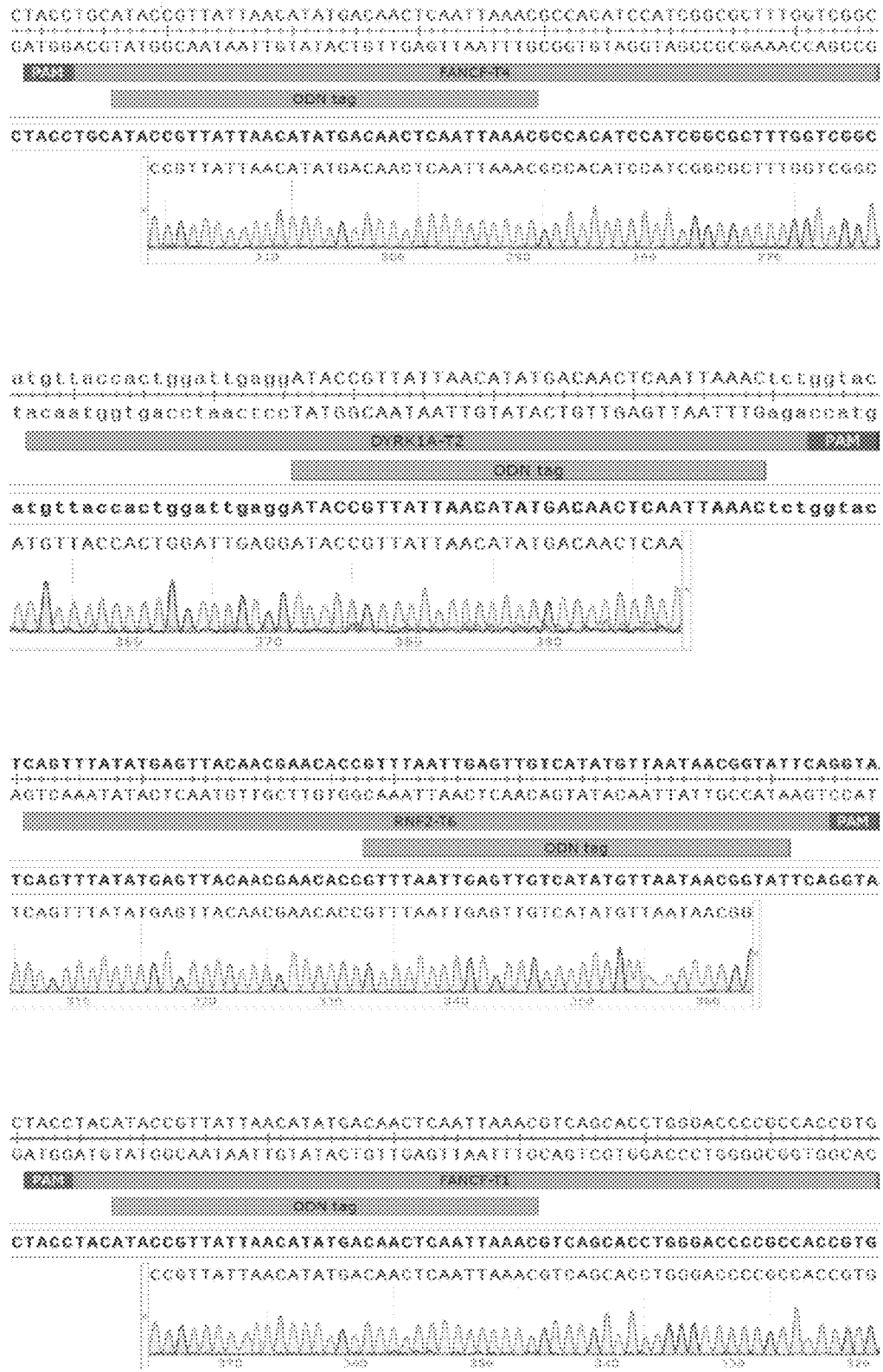

In some embodiments, the FrCas9 according to the disclosure can recognize a variety of DNA double-stranded fragment (DSB) formed by ProSpacer Adjacent Module (PAM) immediately downstream of the targeting sequence. Two important factors are needed for FrCas9 protein to recognize the targeting sequence: one is the nucleotide complementary to crRNA spacer; and the other is the Protospacer Adjacent Motif, PAM) sequence adjacent to the complementary sequence. The depletion experiment shows that FrCas9 has a cleavage effect in the prokaryotic system, and preliminarily verifies that the third and fourth positions of the PAM sequence recognized by this newly discovered Type II CRISPR/Cas9 system are TA, as shown in FIG. 4. It is further confirmed by interference experiment that the PAM downstream of the targeting sequence recognized by FrCas9 is 5'-NNTA-3', as shown in FIGS. 5A-5C. All the above PAMs are verified by eukaryotic experiment, as shown in FIGS. 6A-6B. By artificially designing the spacer sequence in the crRNA, this CRISPR-Cas9 system can target almost all DNA sequences of interest in the genome, producing a site-specific flat-ended double-strand break (DSB). Repair of the DSB by non-homologous termini resulting in small random insertions/deletions (indels) at the cleavage site to inactivate the gene of interest. Alternatively, by high-fidelity homologous repair, precise genomic modifications at the DSB site can be performed using homologous repair templates.

Most human genetic diseases are single base mutation, which cannot be treated by traditional methods. The base editor is one of the latest and most effective ways to achieve accurate genome editing. It is characterized by the use of CRISPR-Cas protein in nicking form to locate specific DNA targets, and the use of DNA deaminase to modify and mutate this DNA target to correct the diseased bases without producing double-stranded DNA fragmentation. In some embodiments, the combination of E796A nFrCas9 with the optimized fourth generation cytidine base editor BE4Gam can successfully construct an E796A nFrCas9-BEGam cytosine base editor (CBE), such that the C:G base pair in DNA can be mutated to T:A. The combination of E796A nFrCas9 with the 7th generation adenine base editor ABE7.10 can successfully construct an E796A nFrCas9-BABE7.10 adenine base editor (ABE), such that the A:T base pair in DNA can be mutated to G:C.

In some embodiments, the specific PAM of FrCas9 of the disclosure is NNTA with a specific target on TATA-BOX (one of the elements constituting the eukaryotic promoter), such that FrCas9 specifically targets TATA-BOX to exert a unique CRISPR interference (CRISPRi)/activation (CRISPRa) effect. Among them, CRISPRi can be achieved by directly targeting the cleavage of TATA-BOX with the active form of FrCas9 and destroying TATA-box, or by directly binding to TATA-box with dFrCas9 (i.e., dead Cas9) without cleavage activity. CRISPRa can be achieved by, but not limited to, dFrCas9-VP64 targeting to the TATA-box site.

Prime Editing (PE) is a brand new accurate genome editing tool. The technology can realize the free replacement of single base and the accurate insertion and deletion of multiple bases, greatly reducing the harmful by-products produced by indels in the process of genome editing and significantly improving the editing accuracy. It is widely considered to be a significant advance in genome editing. In some embodiments, the FrCas9 of the disclosure is fused with a reverse transcriptase, and the corresponding pegRNA can be designed according to its PAM sequence to establish a FrCas9-PE genome editing system. Specifically, two sequences are added to the 3' end sequence of pegRNA. The first sequence is a primer binding site (PBS), which can be complementary to the end of a fractured target DNA chain to initiate a reverse transcription process, and the second sequence is a reverse transcription template (RT template), which carries a target point mutation or insertion deletion mutation to achieve accurate genome editing.

A further purpose of the disclosure is to provide the use of the Type II CRISPR/Cas9 genome editing system derived from *Faecalibaculum rodentium* in editing prokaryotic or eukaryotic genes, CRISPR activation or CRISPR interference.

As a preferred embodiment of the use described according to the disclosure, the Type II CRISPR/Cas9 genome editing system derived from *Faecalibaculum rodentium* is used to bind or cleave structures of DNA function at the DNA level.

Example 1

In the example, the RNA secondary structure of the guide RNA molecule recognized by the Type II CRISPR/Cas9 genome editing system of the *Faecalibaculum rodentium* according to the disclosure was predicted, and the RNA structure after the transcription of the tracrRNA and repeat was predicted by simulating the RNA binding process of the two, and the obtained RNA secondary structure is shown in FIGS. 3A-3F.

(1) Materials: Predicted tracrRNA and repeat sequences, and predicted anti-repeat sequences.
(2) Software: NUPACK (http://www.nupack.org/partition/new)
(3) Prediction method: The in vitro interaction process of 1 µl each of two RNAs at 37° C. was simulated by online application of NUPACK, and the secondary structure of the obtained RNA composition was predicted to obtain an RNA secondary structure as shown in FIG. 2.

As shown in FIGS. 3A-3F, pre-crRNA removed 0 to 16 nts upstream of the spacer sequence and 12 to 29 nts downstream of the repeat sequence under the action of the tracrRNA and Cas9 nuclease to form mature crRNA which was fused with tracrRNA to form a tracrRNA-crRNA complex containing an exogenous DNA sequence complementary to the spacer sequence, and the sequence length was 14 to 30 bps. They were bound to form sgRNA by the addition of a tetraloop of four bases between the downstream of crRNA and the upstream of the tracrRNA, containing two bulge and three duplex structures upstream and three stem loop structures downstream.

Example 2

In the example, the Protospacer Adjacent Motif (PAM) recognized by the Type II CRISPR/Cas9 genome editing system of *Faecalibaculum rodentium* in the prokaryotic system was 5'-NNTA-3'.

(1) Materials: Genes related to the CRISPR/Cas9 genome editing system predicted by the above implementation.
(2) Verification method: In this example, a prokaryotic verification system was constructed for the Type II CRISPR/Cas9 genome editing system of *Faecalibaculum rodentium* according to the disclosure, to verify its cleavage effect and preliminarily explore the recognized PAM sequence by a second generation sequencing technology, and the result is shown in FIG. 4.

Detailed protocols are as follows.
(a) The *Faecalibaculum rodentium* Type II CRISPR/Cas9 genome editing system (comprising an endonuclease Cas9, helper proteins Cas1, Cas2, Csn2, a CRISPR array and a non-coding RNA tracrRNA) of the disclosure was inserted into a pACYC184 vector, wherein the Cas9 protein was subjected to *Escherichia coli* codon optimization. The natural spacer sequences and spacer sequences in library were added into the CRISPR array, and a strong heterologous promoter J23119 was added on the Cas9 protein and the CRISPR array to construct a prokaryotic expression plasmid of pACYC184-Fr-Cas9.
(b) Seven random bases (16,384 insertions in total) were added into the spacer sequence 3' of library. Two restriction endonuclease sites of EcoRI and NcoI were selected from MCS polyclonal of pUC19 vector. The library was cloned into the vector and a target-library plasmid was constructed.
(c) The plasmid containing pACYC184-FrCas9 or empty pACYC184 and target-library were co-electrically transfected to E. coli DH5a. After resuscitation at 25° C. for 2 h, they were uniformly spread on SOB medium containing double resistance of ampicillin sodium (100 µg/mL) and chloramphenicol (34 ug/ml) for incubation at 25° C. for 30 h, and the plasmid was collected by alkaline lysis.
(d) PCR amplification on a region containing a spacer sequence and seven random bases was performed. The secondary sequencing was performed on two ends of a PCR product by adding a linker. The PAM depletion value (PPDV) relative to a no-load control group was calculated. The PAM sequence of the Type II CRISPR/Cas9 genome editing system of the *Faecalibaculum rodentium* was generated by using Weblogo, wherein the PAM sequence is 5'-NNTA-3'.

FIGS. 3A-3F are schematic diagrams of a conservative PAM sequence recognized in a prokaryotic system by the Type II CRISPR/Cas9 genome editing system of *Faecalibaculum rodentium* according to the disclosure. The second-generation sequencing analysis was performed on library DNA obtained through an depletion experiment to calculate the PAM depletion value (PPDV) relative to a no-load control group. The PAM sequence of FrCas9 generated by Weblogo is 5'-NNTA-3'.

Example 3

In the example, the Protospacer Adjacent Motif (PAM) recognized in the Type II CRISPR/Cas9 genome editing system of *Faecalibaculum rodentium* according to the disclosure was verified by an interference experiment, and its cleaving ability at the prokaryotic level and potential genome editing ability in eukaryotes were determined. The results of interference experiments are shown in FIGS. 5A-5C, and the schematic diagrams of various possible PAM sequences recognized by the Type II CRISPR/Cas9 genome editing system of *Faecalibaculum rodentium* according to the disclosure are shown in FIGS. 5A-5C.
(1) Materials: The pACYC184-FrCas9, target-library plasmid obtained in Example 4, and the preliminarily recognized PAM.
(2) Verification method: In the example, the Protospacer Adjacent Motif (PAM) recognized in a prokaryotic system by the Type II CRISPR/Cas9 genome editing system of the *Faecalibaculum rodentium* according to the disclosure was further determined through an interference experiment.
Detailed protocols are as follows.
(a) A total of 16 combined sequences were obtained by adding NNTA to the 3' position of the spacer sequence, and the target plasmid was constructed by cloning into pUC19 through the restriction endonuclease sites of EcoRI and NcoI, respectively.
(b) The 16 target plasmids were respectively transfected into E. coli DH5a electrogenic competence containing FrCas9-related loci, and the plasmids were gradually diluted after resuscitation at 25° C. for 2 h. The target plasmids were incubated overnight at 25° C. in SOB medium containing double resistance of ampicillin sodium (100 ug/ml) and chloramphenicol (34 ug/ml) by dot blot, to observe the number of monoclonal bacteria.

FIGS. 5A-5C are schematic diagrams of an interference experiment of the Type II CRISPR/Cas9 genome editing system of *Faecalibaculum rodentium* according to the disclosure. Based on the NNTA found in the depletion experiment, 16 target plasmids of different combinations of NNs were constructed. The monoclonal colony count was observed through the interference experiment. In FIG. 5A, the leftmost column was designated as the single FrCas9, and the right side was designated as the target plasmid targeted by FrCas9 cleavage. The results showed that the colony count in the right column was decreased. FIG. 5B is a statistical diagram of the cleaving effects of a plurality of PAM sequences recognized by the Type II CRISPR/Cas9 genome editing system of *Faecalibaculum rodentium* according to the disclosure, and the Figure illustrates that cfu of target plasmids of 14 different combinations of NN are decreased as compared with that of the control group. The above results indicated that the Protospacer Adjacent Motif (PAM) recognized by the newly discovered CRISPR/Cas9 system in the prokaryotic system was 5'-NNTA-3' (N represents any base selected from the group consisting of A, T, C and G) by interference experiment.

Example 4

In the example, the tracrRNA range required for cleavage of targeted DNA sequences in the Type II CRISPR/Cas9 genome editing system of *Faecalibaculum rodentium* according to the disclosure was verified by interference experiments, and the results of the interference experiments are shown in FIG. 5C.
(1) Materials: pACYC184-FrCas9, target plasmid, preliminarily recognized PAM obtained in Example 5.
(2) Verification method: In the example, the tracrRNA range required for cleaving the targeted DNA sequence was further determined in a prokaryotic system by the Type II CRISPR/Cas9 genome editing system of *Faecalibaculum rodentium*.
Detailed protocols are as follows.
(a) By a Gibson clone method, a total of six gene sequence of all possible non-coding regions in wild-type *Faecalibaculum rodentium* were cloned into a target plasmid to construct target-NC 1 to 6 plasmids, wherein NC6 is formed by splice the full length of the non-coding regions, and NCs 1 to 5 respectively represent the possible non-coding regions of the first to fifth segments. In each NC plasmid, a strong heterologous promoter J23119 was added upstream of the non-coding region, wherein "+" represented a forward non-coding region and "−" represented a reverse non-coding region, respectively;
(b) From the pACYC184-FrCas9 obtained in Example 5, all possible non-coding regions were removed by a PCR homologous recombination method, and the CRISPR related protein and the CRISPR array gene sequence were retained, thus constructing a pACYC184-AFrCas9;
(c) The 12 target plasmids were respectively transfected into E. coli DH5a electrogenic competence containing pACYC184-AFrCas9, and the plasmids were gradually diluted after resuscitation at 25° C. for 2 h. The target plasmids were incubated overnight at 25° C. in SOB medium containing double resistance of ampicillin sodium (100 ug/ml) and chloramphenicol (34 ug/ml) by dot blot, to observe the number of monoclonal bacteria.

FIG. 5C is a schematic diagram of the interference experiment of the Type II CRISPR/Cas9 genome editing system of *Faecalibaculum rodentium* according to the disclosure, and the results show that the monoclonal colonies of NC1 and NC6 were significantly less than those of NCs 2 to 5, indicating that the alternative non-coding region in the first segment can assist FrCas9 in effectively and targeted cleavage of DNA sequences in *E. coli*.

Example 5

In the example, the ability to cleave targeted DNA sequences in eukaryotic cells was verified by an ODN experiment in the Type II CRISPR/Cas9 genome editing system of *Faecalibaculum rodentium*. An ODN-PCR result is shown in a diagram in FIG. 6A, and a Sanger sequencing result is shown in a diagram in FIG. 6B.

(1) Materials: All amino acid sequences, CRISPR array sequences, tracrRNA sequences, and the recognized PAM of the *Faecalibaculum rodentium* editing gene obtained in Examples 1-6.

(2) Verification method: In the example, the ability to cleave targeted DNA sequences in eukaryotic cells was verified through an ODN experiment in the Type II CRISPR/Cas9 genome editing system of *Faecalibaculum rodentium*.

Detailed protocols are as follows.

(a) The human-derived optimized FrCas9 protein sequence was synthesized and cloned into a PX330 eukaryotic vector to construct a PX330-FrCas9 plasmid.

(b) 30 bps upstream of NGTA, NATA, NCTA and NTTA on a human RNF2 gene were selected as a target sequence. A CRISPR array was constructed by a Gibson method. A human eukaryotic strong promoter U6 was added upstream of the CRISPR array, to construct a PX330-FrCas9-array plasmid.

(c) A mouse-derived eukaryotic strong promoter U6 was added upstream of the tracrRNA determined in Example 4 to construct a PX330-FrCas9-array-tracrRNAplasmid.

(d) The PX330-FrCas9-array-tracrRNA plasmid targeting different gene sites constructed above with 2.5 ug and 1.5 ul ODN was electrically transfected into HEK293T cells in good condition. All the cells were collected after 72 h for extraction of DNA.

(e) The ODN-PCR was performed by designing a pair of primers near the RNF2 targeted gene site and on the ODN sequence, and agarose gel electrophoresis was performed to observe whether there was a band for preliminary identification of the occurrence of targeted cleavage event.

(f) Sanger sequencing verified the successful insertion of ODN into the target site, and confirmed that FrCas9 had the ability to edit the target DNA in eukaryotic cells.

The results of ODN-PCR are shown in FIG. 6A. NGTA, NATA, NCTA and NTTA all had target bands with correct band sizes. As shown in FIG. 8 of Sanger sequencing results, the insertion position of ODN occurred in the 3 to 4 bps base upstream of PAM, indicating that the sequence cleavage range of target gene in FrCas9 was consistent with that in the previous SpCas9.

Example 6

Figure 7A:
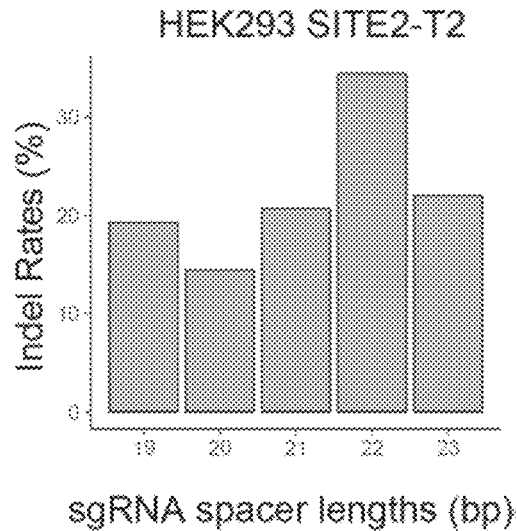
FIGS. 7A-7B are schematic diagrams showing the optimal length of sgRNA in the Type II CRISPR/Cas9 genome editing system of *Faecalibaculum rodentium* according to the disclosure.
Figure 7B:
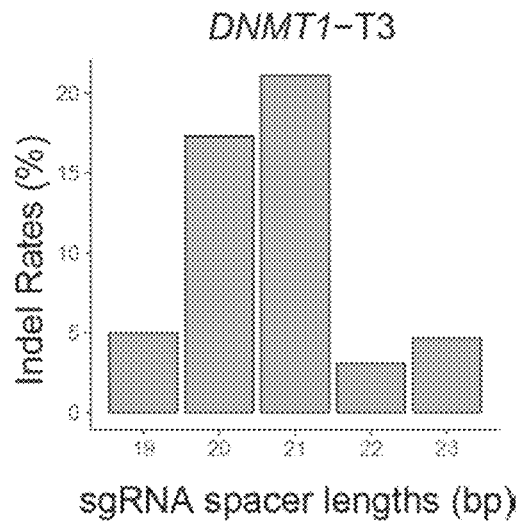
Figure 7C:
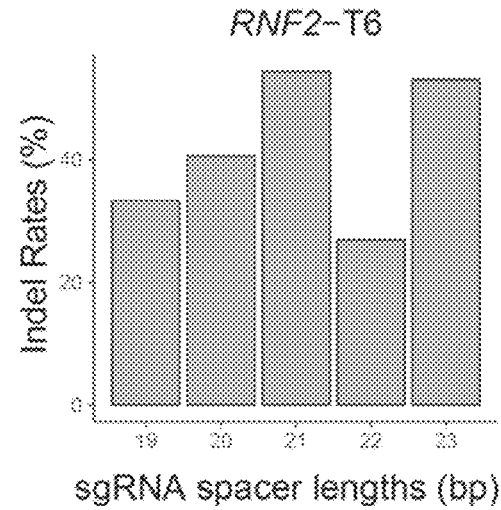
FIG. 7C is a graph showing the cleavage efficiencies of different sgRNA lengths at the RNF2-T6 site.
Figure 8:
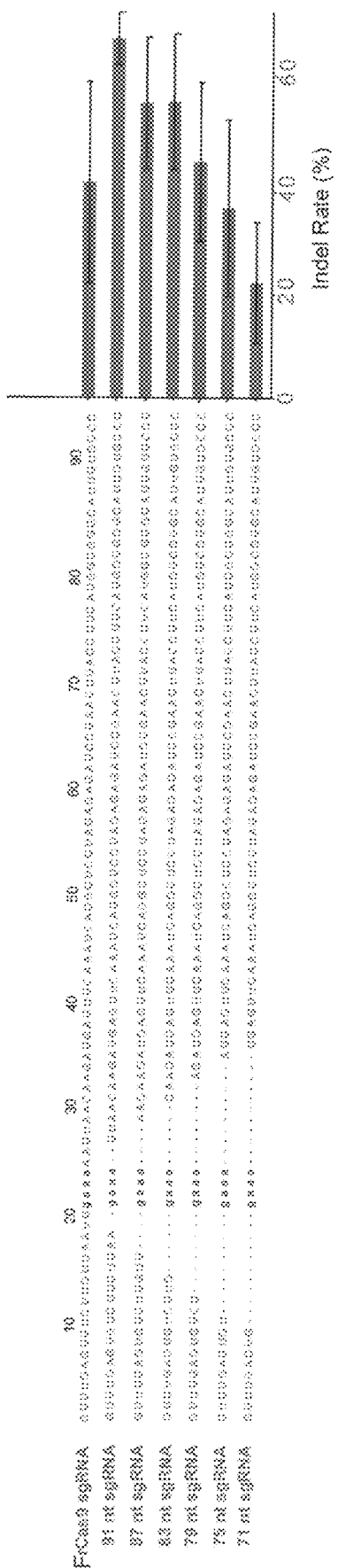
FIG. 8 is a schematic diagram showing the optimal length of the sgRNA recognition sequence of the Type II CRISPR/Cas9 genome editing system of *Faecalibaculum rodentium* according to the disclosure. The sequence of FrCas9 sgRNA is designated SEQ ID NO:9; the sequence of 91 nts sgRNA is designated SEQ ID NO:10; the sequence of 87 nts sgRNA is designated SEQ ID NO:12; the sequence of 83 nts sgRNA is designated SEQ ID NO:14; the sequence of 79 nts sgRNA is designated SEQ ID NO:15; the sequence of 75 nts sgRNA is designated SEQ ID NO:16; and the sequence of 71 nts sgRNA is designated SEQ ID NO:17.

In the example, the optimal length of the sgRNA recognition part in eukaryotic cells in the Type II CRISPR/Cas9 genome editing system of *Faecalibaculum rodentium* according to the disclosure was verified by an ODN experiment, and the results are shown in FIGS. 7A-7C.

(1) Materials: All amino acid sequences, sgRNA sequences and recognized PAM; of the *Faecalibaculum rodentium* editing gene obtained in Examples 1-6; (2) Verification method: In the example, the optimal length of the sgRNA recognition part in the eukaryotic cells in the Type II CRISPR/Cas9 genome editing system of the *Faecalibaculum rodentium* was verified through an ODN experiment.

Detailed protocols are as follows.

(a) The human-derived optimized FrCas9 protein sequence was synthesized and cloned into a PX330 eukaryotic vector to construct a PX330-FrCas9 plasmid.

(b) A target sequence of 30 bp upstream of GGTA near the target site of SpCas9 which was found to have a good cleavage effect in the previous study was selected as the target sequence, and an sgRNA with a recognition length of 19 to 23 bps was constructed by Gibson method. A human eukaryotic strong promoter U6 was added upstream of the sgRNA to construct a PX330-FrCas9-sgRNA plasmid.

(c) The PX330-FrCas9-sgRNA plasmid targeting different gene sites constructed above with 2.5 ug and 1.5 ul ODN was electrically transfected into HEK293T cells in good condition. All the cells were collected after 72 h for extraction of DNA.

(d) The ODN-PCR was performed by designing a pair of primers near the target gene site and on the ODN sequence, and agarose gel electrophoresis was conducted to observe whether there was a band for preliminary identification of targeted cleavage event and to compare the band strength of sgRNA with the recognition length of 19 to 23 bps.

(e) Amplicon high-throughput database was established to quantify the Indel rate of the target region and the cleavage effects of sgRNA with a recognition length of 19 to 23 bps were compared.

As shown in FIGS. 7A-7C, the optimal sgRNA recognition length for FrCas9 was 21 bps, 22 bps, or 23 bps.

Example 7

In the example, the optimal length of an sgRNA scaffold in eukaryotic cells in the Type II CRISPR/Cas9 genome editing system of *Faecalibaculum rodentium* according to the disclosure was verified by an ODN experiment, and the results are shown in FIG. 8.

(1) Materials: All amino acid sequences, sgRNA sequences and recognized PAM; of the *Faecalibaculum rodentium* editing gene obtained in Examples 1-6.

(2) Verification method: in the example, the ODN experiment was used for verifying the optimal length of an sgRNA scaffold of the eukaryotic cells in the Type II CRISPR/Cas9 genome editing system of the *Faecalibaculum rodentium*.

Detailed protocols are as follows.
(a) The human-derived optimized FrCas9 protein sequence was synthesized and cloned into a PX330 eukaryotic vector to construct a PX330-FrCas9 plasmid.
(b) A target sequence of 30 bp upstream of GGTA near the target site of SpCas9 which was found to have a good cleavage effect in the previous study was selected as the target sequence, and an sgRNA with a scaffold length of 71 nts to 95 nts was constructed by Gibson method. A human eukaryotic strong promoter U6 was added upstream of the sgRNA to construct a PX330-FrCas9-sgRNA plasmid.
(c) The PX330-FrCas9-sgRNA plasmid targeting different gene sites constructed above with 2.5 ug and 1.5 ul ODN was electrically transfected into HEK293T cells in good condition. All the cells were collected after 72 h for extraction of DNA.
(d) The ODN-PCR was performed by designing a pair of primers near the targeted gene site and on the ODN sequence, and agarose gel electrophoresis was conducted to observe the presence of bands to preliminarily identify whether targeted cleavage occurred or not, and the band strengths of sgRNA with the scaffold length of 71 nts to 95 nts were compared.
(e) Amplicon high-throughput database was established to quantify the Indel rate of the target region and the cleavage effects of sgRNA with a scaffold length of 71 nts to 95 nts were compared.

As shown in FIGS. 8 and 3, the optimal sgRNA scaffold for FrCas9 is 83 nt to 91 nts.

Example 8

In the example, the cleaving effect in eukaryotic cells in the Type II CRISPR/Cas9 genome editing system of *Faecalibaculum rodentium* as higher than that of SpCas9 and the off-target rate as lower than that of SpCas9 was verified by an ODN experiment.
(1) Materials: All amino acid sequences, 22 bps sgRNA sequence, 5'-GGTA-3' PAM sequence, SpCas9 amino acid sequence, SpCas9 sgRNA sequence and SpCas9 5'-NGG-3' PAM sequence of the *Faecalibaculum rodentium* editing gene obtained in Examples 1-6;
(2) Verification method: In the example, the GUIDE-seq experiment was used to verify that the cleaving effect in eukaryotic cell nuclear cells of the Type II CRISPR/Cas9 genome editing system of *Faecalibaculum rodentium* according to the disclosure was higher than that of SpCas9 and the off-target rate was lower than that of SpCas9.

Detailed protocols are as follows.
(a) The human-derived optimized FrCas9 protein sequence was synthesized and cloned into a PX330 eukaryotic vector to construct a PX330-FrCas9 plasmid.
(b) A target sequence of 30 bp upstream of GGTA near the target site of SpCas9 which was found to have a good cleavage effect in the previous study was selected as the target sequence, and an sgRNA with a recognized length of 22 bp was constructed by Gibson method. A human eukaryotic strong promoter U6 was added upstream of the sgRNA to construct a PX330-FrCas9-sgRNA plasmid, and at the same time, construct a PX330-SpCas9-sgRNA plasmid of 20 bps SpCas9 sgRNA.
(c) The PX330-FrCas9-sgRNA plasmid and PX330-SpCas9-sgRNA plasmid targeting different gene sites constructed above with 2.5 ug and 1.5 ul ODN was electrically transfected into HEK293T cells in good condition. All the cells were collected after 72 h for extraction of DNA.
(d) The ODN-PCR was performed by designing a pair of primers near the targeted gene site and on the ODN sequence, and agarose gel electrophoresis was conducted to observe the presence of bands to preliminarily identify whether targeted cleavage occurred or not, and the DNA with bands was subjected to GUIDE-seq database building.
(e) Through bioinformatics analysis, the target-cleaving effects and off-targets of SpCas9 and FrCas9 at the same site were compared.

Figure 9:
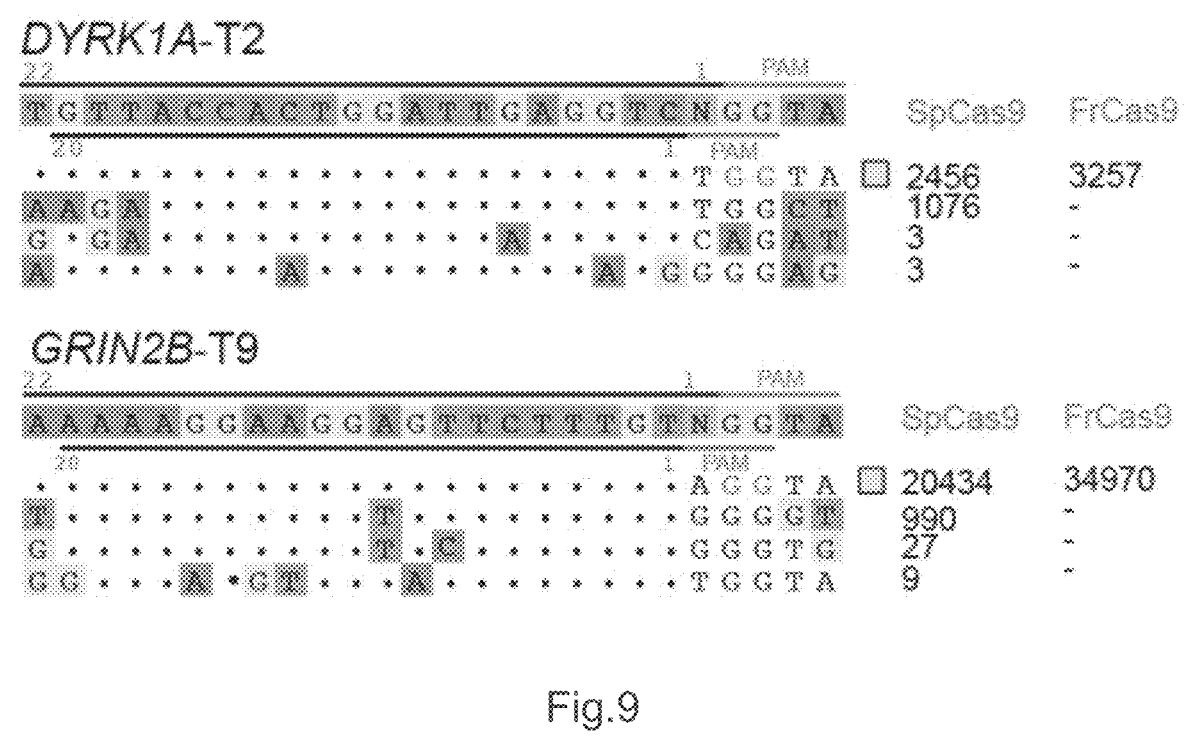

As shown in FIG. 9, FrCas9 was located at target Reads digit 3257 at DYRK1A-T2 site, higher than that of SpCas9 at target Reads 2456. Meanwhile, off-target was not detected for FrCas9, while SpCas9 showed off-target at three sites. FrCas9 was at target Reads digit 34970 at the GRIB2B-T9 site, which was higher than that of SpCas9 at target Reads 20434. Meanwhile, off-target was not detected for FrCas9, while SpCas9 showed off-target at 3 sites. The above data indicated that FrCas9 was a CaS9 protein superior to SpCas9 in cleavage efficiency and specificity.

Example 9 FrCas9 can be Used for Prime Editing (PE)

Most human genetic diseases are single base mutation, which cannot be treated by traditional methods. The base editor is one of the latest and most effective ways to achieve accurate genome editing. It is characterized by the use of CRISPR-Cas protein in nicking form to locate specific DNA targets, and the use of DNA deaminase to modify and mutate this DNA target to correct the diseased bases without producing double-stranded DNA fragmentation. The cytosine base editor (CBE) mutated the C:G base pair in DNA to T:A, and the adenine base editor (ABE) mutated the A:T base pair to G: C.

Figure 10A:
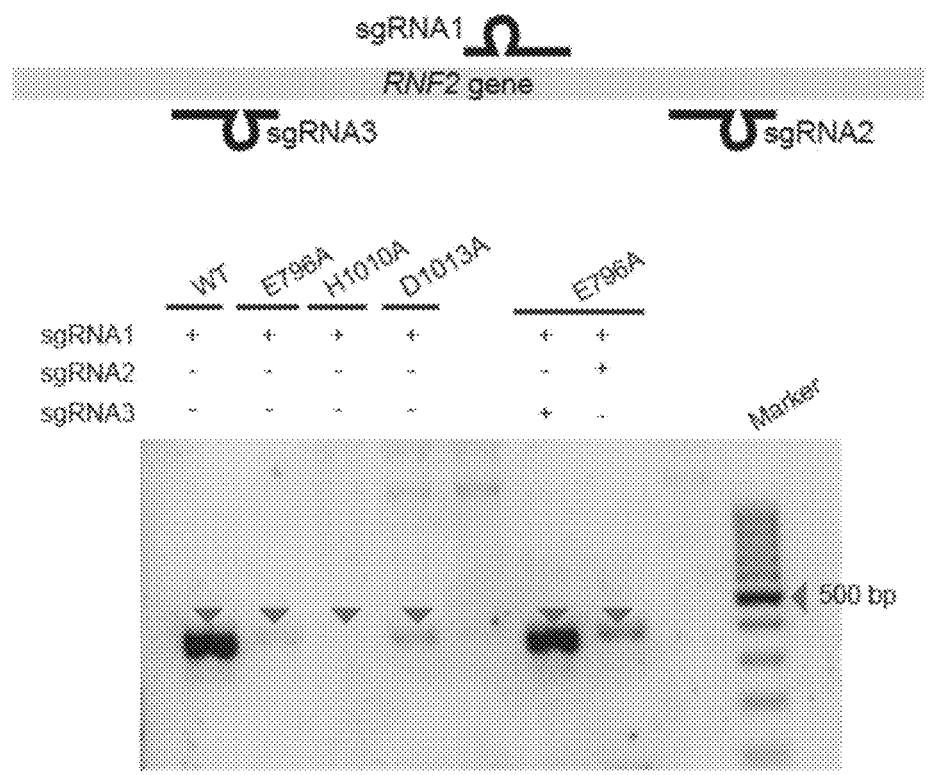
Figure 10B:
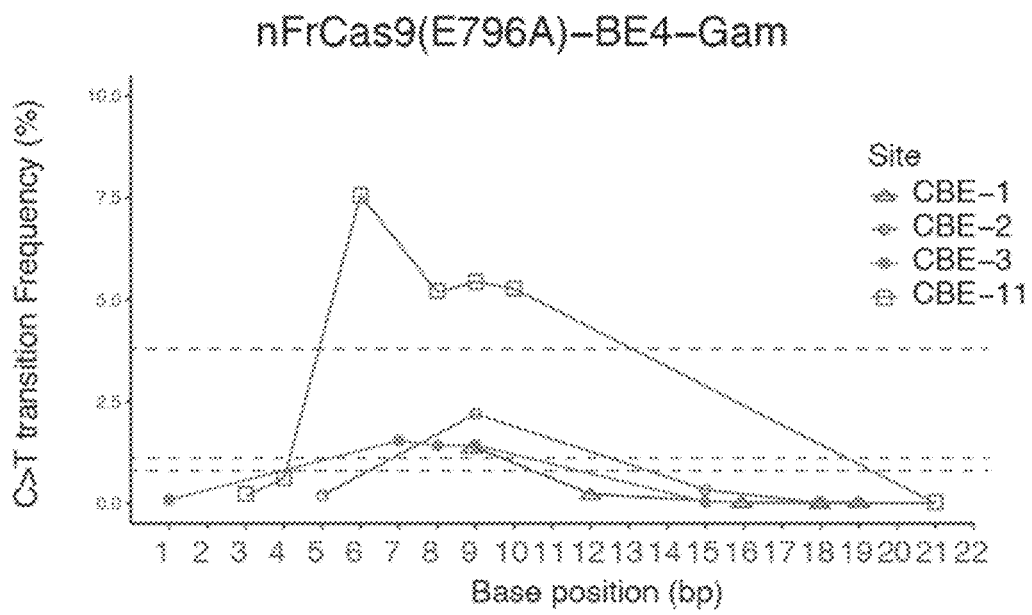
Figure 10C:
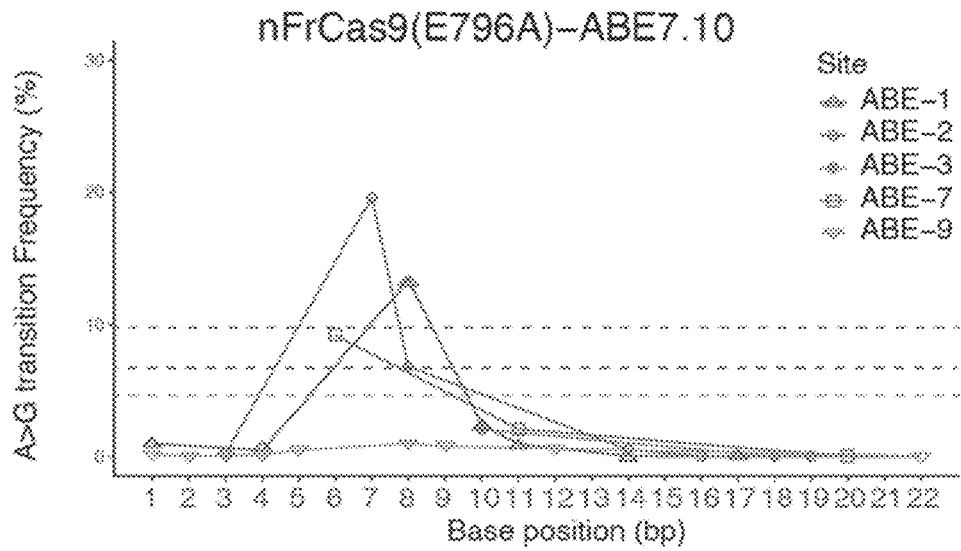
Figure 10D:
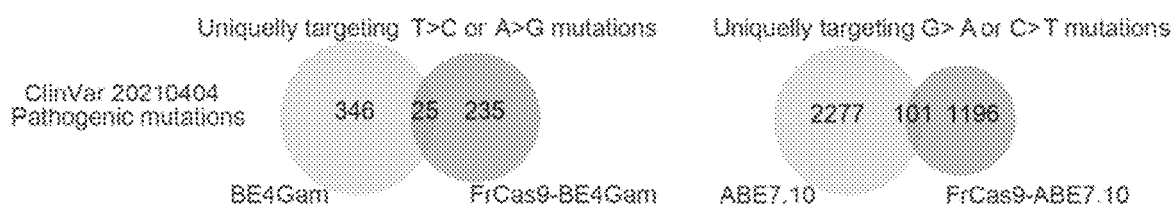

First, three point-mutations of E796A, H1010A and D1013A were respectively incorporated to generate different FrCas9 nickases (nFrCas9) (FIG. 10A). Then, E796A nFrCas9 with the optimized fourth-generation cytidine base editor BE4Gam and seventh-generation adenine base editor ABE7.10 were combined. It is observed that the editing window of FrCas9-BE4Gam was $6^{th}$-$10^{th}$ (FIG. 10B) bases and that of FrCas9-ABE7.10 was $6^{th}$-$8^{th}$ bases (FIG. 10C). Based on the above characteristics, the targeting scopes of FrCas9-BE4Gam and FrCas9-ABE7.10 in ClinVar databases were calculated. For pathogenic mutations that could be precisely corrected by FrCas9-BE4Gam, 90.38% (235/260) unique events were different from SpCas9-BE4Gam. For pathogenic mutations that could be precisely corrected by FrCas9-ABE7.10, 92.21% (1196/1297) unique events were different from SpCas9-ABE7.10 (FIG. 10D). Therefore, the TA-rich PAM of FrCas9 greatly expanded the targets in human genome for base-editor to correct human disease-associated mutations.

Figure 10E:
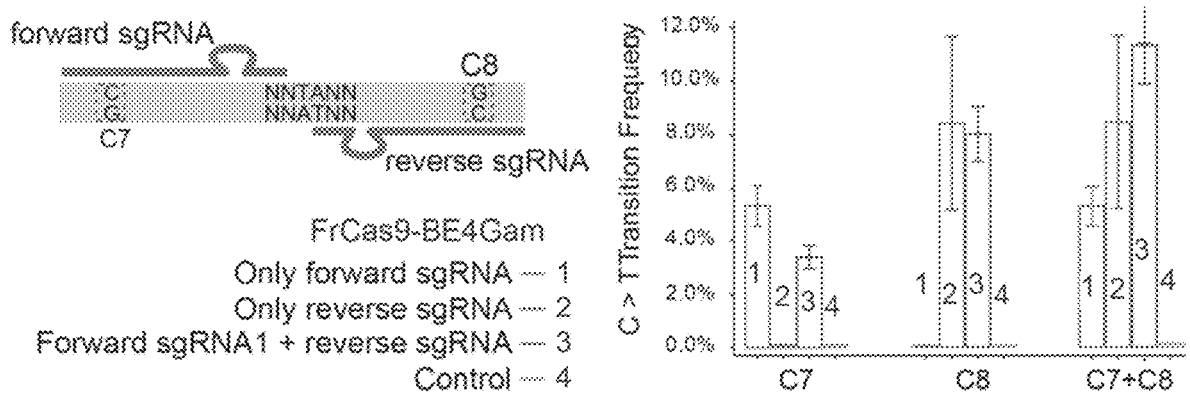
Figure 11A:
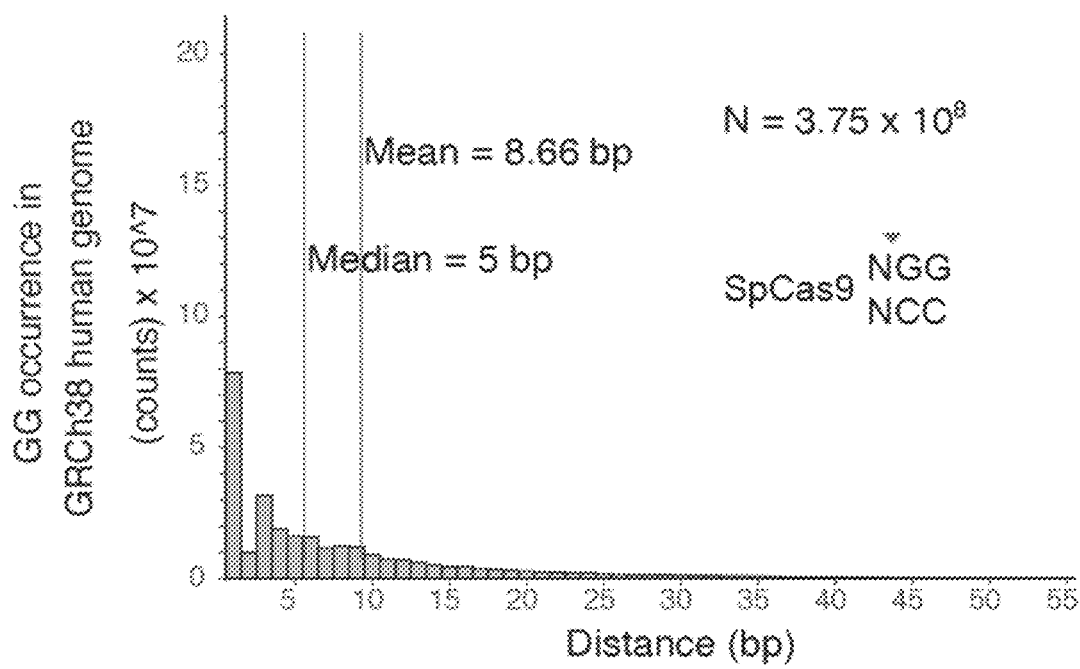
FIGS. 11A-11B are diagrams showing the distribution of FrCas9 and SpCas9 targets in the human genome, where
Figure 11B:
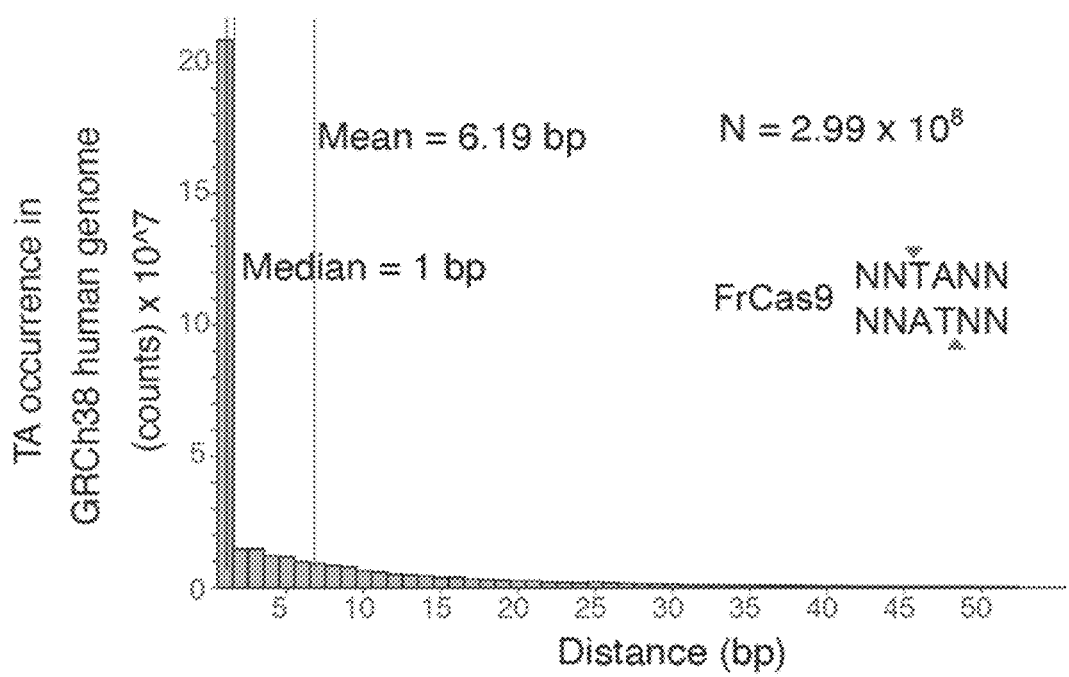

Furthermore, the PAM of FrCas9 (5'-NNTA-3') was palindromic, which offered pairwise "back-to-back" existence of sgRNAs (FIG. 10E). This feature could broaden the scopes of FrCas9 base-editors by modifying two close editing windows at the same time (FIG. 10E) and increase the target distribution and density of FrCas9 sgRNAs. The 5'-GG-3' (represented for SpCas9 PAM) and 5'-TA-3' (represented for FrCas9 PAM) distributions in human genomes were calculated (FIGS. 11A and 11B). Compared to SpCas9 (median=5 bp, mean=8.66 bp)[5], FrCas9 showed more intensive distributions (median=1 bp, mean=6.16 bp) in human genomes, providing additional applicable loci.

Example 10 FrCas9 can Target TATA-Box to Modulate Gene Expression as an Effective Tool for CRISPR Activation and Inhibition TATA-BOX(TATA box/Hogness box) is one of the elements that constitute the promoter of eukaryotes. The consistent order is TATA(A/T)A(A/T) (non-template chain sequence). It is about −30 bp (−25 to-32 bp) upstream of the transcription initiation point of most eukaryotic genes and basically consists of A-T base pairs, which is the selection for determining the transcription initiation of genes. It is one of the binding sites of RNA polymerase, which can only start transcription after firmly binding to TATA-BOX. Since the PAM sequence of FrCas9 is NNTA, it has natural advantages in targeting TATA-BOX.

Figure 12A:
Figure 12B:
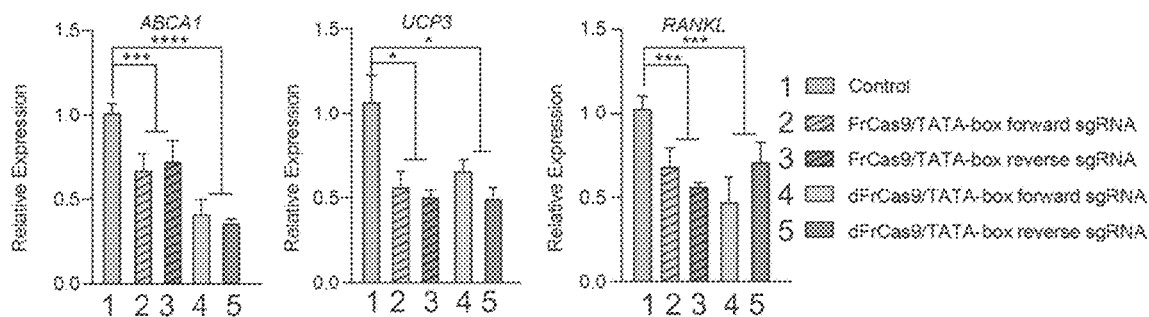

FrCas9 CRISPR interference (CRISPRi) in three TATA-box promoted genes, ABCA1, UCP3 and RANKL were tested (FIG. 12A). By cleaving the TATA-box, FrCas9 reduced ABCA1, UCP3 and RANKL expression by 31.37%, 49.91% and 39.62%, respectively. Meanwhile, dFrCas9 without cleavage activity to directly bind to TATA-box was also utilized, and the expression of ABCA1, UCP3 and RANKL decreased 61.67%, 45.61% and 42.60% by dFrCas9 directly binding to the TATA-box, respectively (FIG. 12B). Accordingly, FrCas9 possesses unique potential for efficient genome engineering of TATA-box related genetic diseases.

Figure 12C:
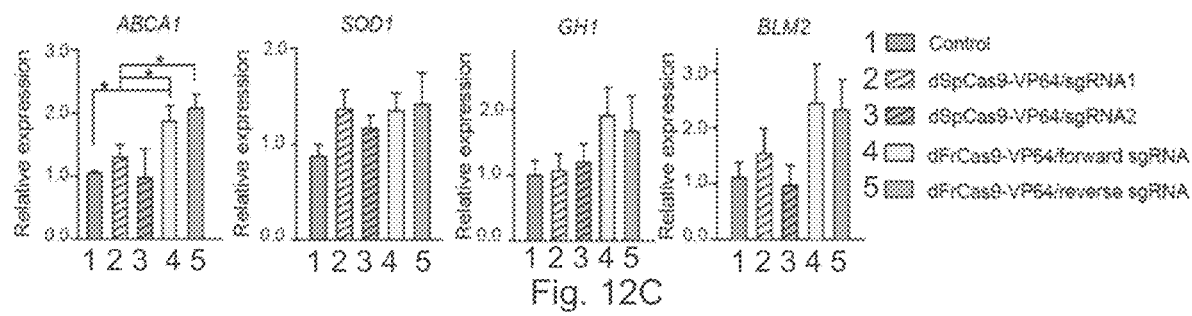

Further, FrCas9 CRISPR activation (CRISPRa) using dFrCas9-VP64 directly targeting the TATA-box was tested, and its performance was compared with dSpCas9-VP64 targeting the upstream of TATA-box. The CRISPRa experiments were conducted in ABCA1, SOD1, GH1 and BLM2 genes. The results showed that dFrCas9-VP64 enables effective transcriptional activation. Moreover, the fold activation of dFrCas9-VP64 in ABCA1, GH1 and BLM2 was higher than that of dSpCas9-VP64, while the fold activation of SOD1 gene was comparable to that of dSpCas9-VP64 (FIG. 12C). Therefore, FrCas9 is a promising tool for CRISPR screening due to its unique 5'-NNTA-3' PAM.

Example 11 FrCas9 can be Used for Prime Editing, PE

Figure 13:
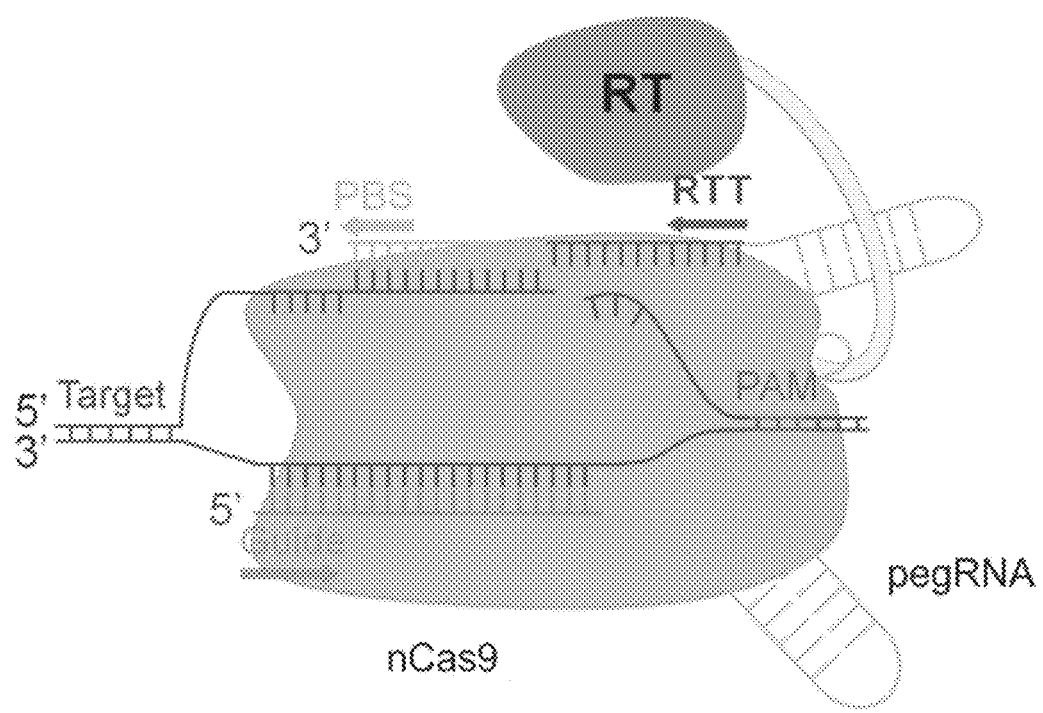
FIG. 13 is a schematic diagram of the Prime Editing genome editing system.

Prime Editing (PE) is a brand-new precise gene editing tool. This technology can greatly reduce the harmful by-products produced by indels during the gene editing process, significantly improve the editing accuracy, and has the potential to overcome fundamental barriers to the treatment of genetic diseases with existing gene editing methods. The PE system consists of two components, which comprises an engineered guide RNA (pegRNA) and a prime editor protein. pegRNAs have dual functions: the capable of directing the edited protein to the target site and containing the edited template sequence. The prime editor protein consists of a mutated Cas9 nickase (which cuts only one DNA strand) and a reverse transcriptase fused. After Cas9 cleaves the target site, reverse transcriptase uses the pegRNA as a template for reverse transcription, thereby incorporating the desired edit into the DNA strand, and the corrected sequence preferentially replaces the original genomic DNA, thereby permanently editing the target site (FIG. 13).

Based on the biological characteristics of FrCas9, FrCas9 with reverse transcriptase was fused, and the corresponding pegRNA was designed according to its PAM sequence, and the FrCas9-PE gene editing system was established, and its gene editing efficiency was optimized. The pegRNA was designed according to the FrCas9 PAM sequence. Compared with sgRNA, the 3'-end sequence of pegRNA has two additional sequences. The first sequence is the primer binding site (PBS), which can be complementary to the end of the broken target DNA strand to initiate reverse transcription. In the process, the second sequence is a reverse transcription template (RT template), which carries target point mutations or indel mutations to achieve precise gene editing. Previous studies have shown that the length of the PBS and RT template sequences will significantly affect the gene editing efficiency of the PE system, and it varies by gene locus. Therefore, we explored the optimization of editing efficiency through the combination of PBS and RT template sequences of different lengths.

Figure 14:
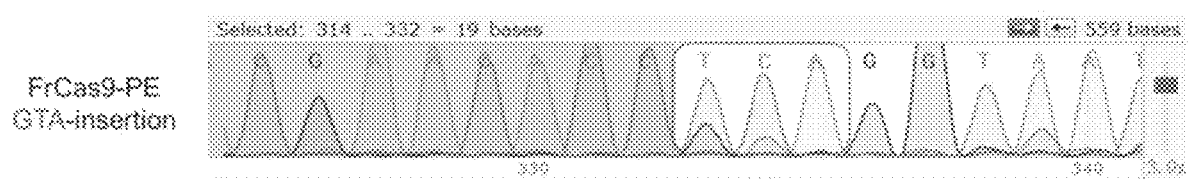
FIG. 14 shows the genome editing effect of the FrCas9-PE Prime Editing system verified by Sanger sequencing, wherein the measured sequence was CGAACACT-CAAGGTAAT (SEQ ID NO: 33).

At the cellular level, the gene editing effect of the FrCas9-PE system was preliminarily verified. In HEK293T cells, the HEK293T-RNF2 gene locus, which is commonly used for CRISPR gene editing efficiency evaluation, was targeted to verify the gene editing function of the FrCas9-PE system. Our current experimental results show that FrCas9-PE can produce site-specific base editing effects. After that, we will further transform the existing FrCas9-PE, including codon optimization, nuclear localization sequence position and number optimization, reverse transcriptase modification, etc (FIG. 14).

---

What are claimed:

1. A Type II CRISPR/Cas9 genome editing composition, wherein the Type II CRISPR/Cas9 genome editing composition comprises a Cas9 protein, helper proteins, a crRNA (CRISPR RNA) and a tracrRNA (trans-activated CRISPR RNA) in the functional form of an RNP complex (ribonucleoprotein complex) of the Cas9 protein and a guide RNA formed by hybridizing the crRNA with the tracrRNA;

wherein the Cas9 protein is a DNA endonuclease, and the Cas9 protein comprises an amino acid sequence of SEQ ID NO: 1;

wherein the CRISPR RNA is generated by transcription of a CRISPR Array, and comprises an RNA sequence of SEQ ID NO: 5;

wherein the trans-activated CRISPR RNA comprises a sequence complementary to a direct repeat sequence of the CRISPR RNA, and the trans-activated CRISPR RNA comprises a nucleic acid sequence of SEQ ID NO: 8; and wherein the guide RNA formed by hybridizing the crRNA with the tracrRNA comprises a scaffold composed of a sequence of 7 to 24 nts of a crRNA direct repeat sequence and a tracrRNA sequence; wherein the two parts are fused by a "GAAA", "TGAA", or "AAAC" linker to form an sgRNA scaffold; and wherein a protospacer adjacent motif sequence, required for binding to or cleaving DNA, is 5'-NNTA-3' and is located downstream of the guide RNA/sgRNA recognition sequence, wherein N is A, T, C or G.

2. The Type II CRISPR/Cas9 genome editing composition according to claim 1, wherein the Cas9 protein cleaves a double-stranded DNA complementary to a crRNA upstream of a PAM sequence by a nuclease domain, wherein the nuclease domain is selected from a HNH-like nuclease domain, a RuvC-like nuclease domain, or a combination thereof.

3. The Type II CRISPR/Cas9 genome editing composition according to claim 1, wherein the helper proteins comprise a Cas1 helper protein, a Cas2 helper protein and a Csn2 helper protein;

wherein the Cas1 helper protein comprises an amino acid sequence of SEQ ID NO: 2;

wherein the Cas2 helper protein comprises an amino acid sequence of SEQ ID NO: 3;

wherein the Csn2 helper protein comprises an amino acid sequence of SEQ ID NO: 4.

4. The Type II CRISPR/Cas9 genome editing composition according to claim 1, wherein the CRISPR Array comprises a direct repeat sequence and a spacer sequence, wherein the direct repeat sequence comprises a nucleic acid sequence of SEQ ID NO: 6; and wherein the spacer sequence comprises a nucleic acid sequence of SEQ ID NO: 7.

5. The Type II CRISPR/Cas9 genome editing composition according to claim 1, wherein an sgRNA scaffold formed by fusion of the crRNA direct repeat sequence of 20 nts and a full length sequence of the tracrRNA by "GAAA" is of or a variant thereof selected from the following five scaffolds:

(1) an sgRNA scaffold with a length of 91 nts, which comprises 18 nts direct repeat sequence and 69 nts tracrRNA, of SEQ ID NO: 10;

(2) an sgRNA scaffold with a length of 89 nts, which comprises 17 nts direct repeat sequence and 68 nts tracrRNA, of SEQ ID NO: 11;

(3) an sgRNA scaffold with a length of 87 nts, which comprises 16 nts direct repeat sequence and 67 nts tracrRNA, of SEQ ID NO: 12;

(4) an sgRNA scaffold with a length of 85 nts, which comprises 15 nts direct repeat sequence and 66 nts tracrRNA, of SEQ ID NO: 13 and (5) an sgRNA scaffold with a length of 83 nts, which comprises 14 nts direct repeat sequence and 65 nts tracrRNA, of SEQ ID NO: 14.

6. The Type II CRISPR/Cas9 genome editing composition according to claim 1, wherein the Type II CRISPR/Cas9 genome editing composition is derived from *Faecalibaculum rodentium*, and wherein the length of a paired binding part of the guide RNA and a target of a specific DNA ranges from 14 to 30 bps;

wherein the specific DNA is a DNA of prokaryote or eukaryote.

7. The Type II CRISPR/Cas9 genome editing composition according to claim 6, wherein the length of the paired binding part is 21 bps, 22 bps or 23 bps, and wherein the RNP complex is highly sensitive to base mismatch of 14 bps close to a protospacer adjacent motif and the 14 bps is a seed region.

8. A genome editing tool, comprising:

the Type II CRISPR/Cas9 genome editing composition according to claim 1, wherein the genome editing tool is a base editor.

9. A genome editing tool, comprising:

the Type II CRISPR/Cas9 genome editing composition according to claim 2, wherein the genome editing tool is a base editor.

* * * * *